US008106428B2

(12) United States Patent  
Koh et al.

(10) Patent No.: US 8,106,428 B2
(45) Date of Patent: Jan. 31, 2012

(54) NANO-SCALE BRIDGE BIOSENSORS

(75) Inventors: Seong Jin Koh, Mansfield, TX (US); Hong-Wen Huang, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 85 days.

(21) Appl. No.: 12/716,109

(22) Filed: Mar. 2, 2010

(65) Prior Publication Data

US 2010/0227416 A1 Sep. 9, 2010

Related U.S. Application Data

(60) Provisional application No. 61/157,053, filed on Mar. 3, 2009.

(51) Int. Cl.
*H01L 51/10* (2006.01)
*H01L 51/30* (2006.01)
*G01N 33/53* (2006.01)
*C12Q 1/68* (2006.01)
*C12M 1/34* (2006.01)

(52) U.S. Cl. .................. 257/253; 257/E51.023; 438/49; 435/6.1; 435/7.1; 435/283.1

(58) Field of Classification Search ............. 257/253; 438/49; 977/924; 435/6.1, 7.1, 283.1
See application file for complete search history.

(56) References Cited

U.S. PATENT DOCUMENTS

| 5,472,881 A | 12/1995 | Beebe et al. |
| 5,837,832 A | 11/1998 | Chee et al. |
| 6,506,564 B1 | 1/2003 | Mirkin et al. |
| 6,656,693 B2 | 12/2003 | Saraf et al. |
| 6,958,216 B2 | 10/2005 | Kelley et al. |
| 7,465,953 B1 | 12/2008 | Koh et al. |
| 7,507,530 B2 | 3/2009 | Huang et al. |
| 7,625,702 B2 | 12/2009 | Cha |
| 2002/0098500 A1 | 7/2002 | Saraf et al. |
| 2003/0134433 A1 | 7/2003 | Gabriel et al. |
| 2004/0132070 A1 | 7/2004 | Star et al. |
| 2004/0191801 A1 | 9/2004 | Heeger et al. |
| 2006/0134657 A1 | 6/2006 | Hodko et al. |
| 2006/0194228 A1 | 8/2006 | Rakitin et al. |
| 2006/0246482 A1 | 11/2006 | Ford et al. |
| 2007/0178477 A1 | 8/2007 | Joiner, Jr. et al. |
| 2008/0094078 A1 | 4/2008 | So et al. |

FOREIGN PATENT DOCUMENTS

| CN | 1525163 A | 9/2004 |
| CN | 1844907 A | 10/2006 |
| CN | 101078026 A | 11/2007 |
| WO | WO 2006024023 | 3/2006 |

OTHER PUBLICATIONS

Aerts, Wouter F. et al., "Design of an Organic Pixel Addressing Circuit for an Active-Matrix OLED Display", IEEE Transactions on Electron Devices Dec. 2002, vol. 49, No. 12, 2124-2130.

(Continued)

*Primary Examiner* — Evan Pert
(74) *Attorney, Agent, or Firm* — Kilpatrick Townsend & Stockton LLP

(57) ABSTRACT

Devices, systems, and methods for detecting nucleic acid hybridization, including single nucleic base mutations at low concentrations, are disclosed, using capture units having nanoparticles with attached single-stranded oligonucleotides that are capable of hybridizing target oligonucleotides and reporter molecules having nanoparticles with attached single-stranded oligonucleotides, without the use of labeling or target modification.

25 Claims, 16 Drawing Sheets

OTHER PUBLICATIONS

Ahmadi, Temer S. et al., "Shape-Controlled Synthesis of Colloidal Platinum Nanoparticles", Science Jun. 28, 1996, vol. 22; 1924-1926.
Allara, David L. et al., "Spontaneously Organized Molecular Assemblies. 1. Formation, Dynamics, and Physical Properties of n-Alkanoic Acids Adsorbed from Solution on an Oxidized Aluminum Surface", Langmuir 1985, 1:45-52.
Bahnemann, D. W. "Mechanisms of Organic Transformations on Semiconductor Particles", Photochemical Conversion and Storage of Solar Energy 1991, 251-276.
Beaucage, S.L. et al., "Deoxynucleoside Phosphoramidites—A New Class of Key Intermediates for Deoxypolynucleotide Synthesis", Tetrahedron Letters 1981, vol. 22, No. 20, pp. 1859-1862.
Benn, James A. et al., "Comparative modeling and analysis of microfluidic and conventional DNA microarrays", Analytical Biochemistry 2006, 348: 284-293.
Braun, Erez et al., "DNA-templated assembly and electrode attachment of a conducting silver wire", Nature Feb. 19, 1998, vol. 391; 775-778.
Brus, L. "Quantum Crystallites and Nonlinear Optics", Appl. Phys. Sep. 27, 1991, A53: 465-474.
Burwell, Robert L. "Modified silica gels as adsorbents and catalysts", Chemtech Jun. 1974, 370-377.
Cervera, Javier et al., "Synchronization of coupled single-electron circuits based on nanoparticles and tunneling junctions", Journal of Applied Physics Apr. 1, 2009, vol. 105, Issue 7, Article No. 074315.
Curtis, Andrew C. et al., "A Morphology-Selective Copper Organosol", Angew. Chem. Int. Ed. Engl. 1988, vol. 27, No. 11, pp. 1530-1533.
De, Mrinmoy et al., "Applications of Nanoparticles in Biology", Advanced Materials 2008, 20, 4225-4241.
Du, Xiaoyan et al., "DNA Biosensors prepared using platinum nanoparticle-deposited glassy carbon electrodes", Sensor Letters Feb. 2008, vol. 6, Issue 1, 226-230 (Abstract only).
Eltekova, Nina A. et al., "Adsorption of Aromatic Compounds from Solutions on Titanium Dioxide and Silica", Langmuir 1987, 3: 951-957.
Grabar, Katherine C. et al., "Preparation and Characterization of Au Colloid Monolayers", Analytical Chemistry Feb. 15, 1995, vol. 67, No. 4, 735-473.
Hassibi, Arjang et al., "A Programmable 0.18-um CMOS Electrochemical Sensor Microarray for Biomolecular Detection", IEEE Sensors Journal Dec. 2006, vol. 6, No. 6, 1380-1388.
Hassibi, Arjang "Integrated Microarrays", Doctoral Thesis Jun. 2005.
Henglein, Arnim "Small-Particle Research: Physicochemical Properties of Extremely Small Colloidal Metal and Semiconductor Particles", Chem. Rev 1989, 89: 1861-1873.
Henglein, A. et al., "Absorption Spectrum and Some Chemical Reactions of Colloidal Platinum in Aqueous Solution", J. Phys. Chem. 1995, 99: 14129-14136.
Henglein, Arnim "Mechanism of Reactions on Colloidal Microelectrodes and Size Quantization Effects", Topics in Current Chemistry 1988, vol. 143; pp. 113-180.
Hickman, James J. et al., "Combining Spontaneous Molecular Assembly with Microfabrication to Pattern Surfaces: Selective Binding of Isonitriles to Platinum Microwires and Characterization by Electrochemistry and Surface Spectroscopy", J. Am. Chem. Soc. 1989, 111: 7271-7272.
Huang, Hong-Wen et al., "Single-particle placement via self-limiting electrostatic gating", Applied Physics Letters 2008, 93:073110-1.
Hubbard, Arthur T. "Electrochemistry of Well-Defined Surfaces", Acc. Chem. Res. 1980, 13: 177-184.
Huo, Fengwei et al., "Asymmetric Functionalization of Nanoparticles Based on Thermally Addressable DNA Interconnects", Advanced Materials 2006, 18, 2304-2306.
Iler, "The Surface Chemistry of Silica", The Chemistry of Silica 1979, Chapter 6: 622-729.
Koh, Seong J. "Controlled Placement of Nanoscale Building Blocks: Toward Large-Scale Fabrication of Nanoscale Devices", JOM Mar. 2007, 59: 22-28.
Koh, Seong J. "Strategies for Controlled Placement of Nanoscale Building Blocks", Nanoscale Research Letters 2007, 2: 519-545.
Lee, Haiwon et al., "Adsorption of Ordered Zirconium Phosphonate Multilayer Films on Silicon and Gold Surfaces", J. Phys. Chem. 1988, 92: 2597-2601.
Lee, Hye J. et al., "SPR Imaging Measurements of 1-D and 2-D DNA Microarrays Created from Microfluidic Channels on Gold Thin Films", Anal. Chem. 2001, 73: 5525-5531.
Li, Yongxin et al., "Covalent immobilization of single-walled carbon nanotubes and single-stranded deoxyribonucleic acid nanocomposites on glassy carbon electrode: Preparation, characterization, and applications", Talanta Dec. 15, 2008, vol. 77, Issue 2, 833-838 (Abstract only).
Lin, Yung-Chen et al., "Self-Aligned Nanolithography in a Nanogap", Nano Letters Jun. 2009, vol. 9, Issue 6, 2234-2238 (Abstract only).
Ma, Liang-Chieh et al., "Electrostatic Funneling for Precise Nanoparticle Placement: A Route to Wafer-Scale Integration", Nano Letters 2007, vol. 7, No. 2, 439-445.
Maoz, Rivka et al., "Penetration-Controlled Reactions in Organized Monolayer Assemblies. 2. Aqueous Permanganate Interaction with Self-Assembling Monolayers of Long-Chain Surfactants", Langmuir 1987, 3: 1045-1051.
Maoz, Rivka et al., "Penetration-Controlled Reactions in Organized Monolayer Assemblies. 2. Aqueous Permanganate Interaction with Self-Assembling Monolayers of Long-Chain Surfactants", Langmuir 1987, 3: 1034-1044.
Massart, Rene "Preparation of Aqueous Magnetic Liquids in Alkaline and Acidic Media", IEEE Transactions on Magnetics Mar. 1981, vol. Mag-17, No. 2, pp. 1247-1248.
Matteucci, M. D. et al., "Synthesis of Deoxyoligonucleotides on a Polymer Support", J. Am. Chem. Soc. 1981, 103: 3185-3191.
Moreno, M. et al., "Selective immobilization of oligonucleotide-modified gold nanoparticles by electrodeposition on screen-printed electrodes", Biosensors & Bioelectronics Dec. 15, 2009, vol. 25, Issue 4, 778-783 (Abstract only).
Mucic, C. et al., "DNA-Directed Synthesis of Binary Nanoparticle Network Materials", J. Am. Chem. Soc. 1998, 120, 12674-12675.
Nam, Jwa-Min et al., "Nanoparticle-Based Bio-Bar Codes for the Ultrasensitive Detection of Proteins", Science Sep. 26, 2003, vol. 301, 1884-1886.
Nuzzo, Ralph G. et al., "Spontaneously Organized Molecular Assemblies. 3. Preparation and Properties of Solution Adsorbed Monolayers of Organic Disulfides on Gold Surfaces", J. Am. Chem. Soc. 1987, 109: 2358-2368.
Olshavsky, M. A. et al., "Organometallic Synthesis of GaAs Crystallites Exhibiting Quantum Confinement", J. Am. Chem. Soc. 1990, 112: 9438-9439.
Rakitin, A et al., "Metallic conduction through engineered DNA: DNA nanoelectronic building blocks.", Phys Rev Lett Apr. 16, 2001, 86(16):3670-3.
Ray, Vishva et al., "CMOS-compatible fabrication of room-temperature single-electron devices", Nature Nanotechnology Oct. 2008, vol. 3, 603-608.
Soriaga, Manuel P. et al., "Determination of the Orientation of Aromatic Molecules Adsorbed on Platinum Electrodes. The Effect of Solute Concentration", J. Am. Chem. Soc. 1982, 104: 3937-3945.
Timmons, C. O. et al., "Investigation of Fatty Acid Monolayers on Metals by Contact", The Journal of Physical Chemistry Mar. 1965, vol. 69, No. 8, 984-990.
Tompkins, Harland G. et al., "The Study of the Gas-Solid Interaction of Acetic Acid with a Cuprous Oxide Surface Using Reflection-Absorption Spectroscopy", Journal of Colloid and Interface Science Dec. 1974, vol. 49, No. 3, 410-421.
Uchida, Hiroyki et al., "GaAs Nanocrystals Prepared in Quinoline", The Journal of Physical Chemistry 1991, vol. 95, No. 14, 582-584.
Wang, Y. et al., "Nanometer-Sized Semiconductor Clusters: Materials Synthesis, Quantum Size Effects, and Photophysical Properties", J. Phys. Chem. 1991, 95: 525-532.
Wang, Lijiang et al., "The *Escherichia coli* O157 : H7 DNA detection on a gold nanoparticle-enhanced piezoelectric biosensor", Chinese Science Bulletin Apr. 2008, vol. 53, Issue 8, 1175-1184 (Abstract only).

Wasserman, Stephen R. et al., "Structure and Reactivity of Alkylsiloxane Monolayers Formed by Reaction of Alkyltrichlorosilanes on Silicon Substrates", Langmuir 1989, 5: 1074-1087.

Wei, Cheng-Wey et al., "Using a microfluidic device for 1 µl DNA microarray hybridization in 500 s", Nucleic Acids Research 2005, vol. 33, No. 8, e78.

Weller, Horst "Colloidal Semiconductor Q-Particles: Chemistry in the Transition Region Between Solid State and Molecules", Angew. Chem. Int. Ed. Engl. 1993, 32: 41-53.

Whitesides, George M. et al., "Self-Assembled Monolayers and Lithography", Proceedings of the Robert A. Welch Foundation 39th Conference on Chemical Research Nanophase Chemistry, Houston TX 1995, 109-121.

Xu, Xiaoyang et al., "Asymmetric Functionalization of Gold Nanoparticles with Oligonucleotides", J. Am. Chem. Soc. 2006, 128, 9286-9287.

Zhao, Jing et al., "Self-assembled multilayer of gold nanoparticles for amplified electrochemical detection of cytochrome c", Analyst Sep. 2008, vol. 33, Issue 9, 1242-1245 (Abstract only).

```
                            SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Unknown construct
<220> FEATURE:
<221> NAME/KEY: misc_feature
<222> LOCATION: (1)..(1)
<220> FEATURE:
<221> NAME/KEY: misc_feature
<222> LOCATION: (1)..(1)
<223> OTHER INFORMATION: thiol hexamethylene linker

<400> SEQUENCE: 1
ccatccataa gtctgcctaa taag                                          24

<210> SEQ ID NO 2
<211> LENGTH: 24
<212> TYPE: DNA
<213> ORGANISM: Artificial Sequence
<220> FEATURE:
<223> OTHER INFORMATION: Unknown construct

<400> SEQUENCE: 2
tacgagttga gaatcctgaa tgcg                                          24

<210> SEQ ID NO 3
<211> LENGTH: 36
<212> TYPE: DNA
<213> ORGANISM: Artificial Sequence
<220> FEATURE:
<223> OTHER INFORMATION: Unknown construct

<400> SEQUENCE: 3
ggtaggtatt cagacggatt attcatgctc aactct                             36

<210> SEQ ID NO 4
<211> LENGTH: 12
<212> TYPE: DNA
<213> ORGANISM: Artificial Sequence
<220> FEATURE:
<223> OTHER INFORMATION: Unknown construct
<220> FEATURE:
<221> NAME/KEY: misc_feature
<222> LOCATION: (12)..(12)
<220> FEATURE:
<221> NAME/KEY: misc_feature
<222> LOCATION: (12)..(12)
<223> OTHER INFORMATION: thiol hexamethylene linker
```

```
<400> SEQUENCE: 4
taggacttac gc                                                      12
```

NANO-SCALE BRIDGE BIOSENSORS

CROSS REFERENCE TO RELATED APPLICATIONS

This application claims the benefit of U.S. Application No. 61/157,053, filed Mar. 3, 2009, the disclosure of which is incorporated herein by reference in its entirety.

REFERENCE TO GOVERNMENT GRANTS

Portions of the disclosure herein may have been supported, in part, by a grant from the National Science Foundation (Award No. ECCS-0925997). The United States Government may have certain rights in this application.

FIELD OF THE INVENTION

The invention relates generally to devices, systems, and methods for detecting nucleic acid hybridization, including single nucleic base mutations, are disclosed, using capture units having nanoparticles with attached single-stranded oligonucleotides that is capable of hybridizing target oligonucleotides and reporter molecules having nanoparticles with attached single-stranded oligonucleotides, without the use of labeling or target modification.

BACKGROUND OF THE INVENTION

Individual genetic mutations can predispose a cell or tissue toward certain diseases, such as most cancers, cystic fibrosis, and sickle cell anemia. Specific mutations in such genes can thus be used as diagnostic indicators for the susceptibility of disease, aiding in early detection and treatment. The high-throughput detection of genes has been studied for several years and devices like microarrays and the DNA chip have significantly increased our capabilities.

The basic principle of microacrray technology requires tagging of the sample with fluorescent dyes. However, these modifications can change the thermodynamic properties of the molecular interactions of DNA and, in some cases, unnaturally stabilize or destabilize the DNA double-strand and change the melting temperature significantly. Additionally, expensive fluorescent microscopes are needed to visualize the data and normalization of the data to references remains problematic. Further, the hybridization of the probe and target molecules is a diffusion-limited process requiring long-incubation times as the target molecules must travel to the arrayed probes on the surface of the chip. The fluorophores are also known to have great effect on the stability of the duplexes as a function of the sequence itself. In addition, fluorescent dyes photobleach, quench statically, or interact with each other, so the microarray technologists need to have very detailed knowledge about the limitations of the optics, reagents used, and the sample interactions.

Several silicon-based approaches have been reported for chemical and biological sensing. While many of the silicon-based sensors can be fabricated with compact size, none of these efforts have resulted in a portable sensor with adequate performance. The hybridization of DNA with probe-functionalized chip surfaces has been studied for biophysical characterization and kinetics studies but its use in a functional nano-scale device has not been reported. The challenges range from the costly and lengthy fabrication processes to the need for external expensive measurement equipment. The DNA hybridization detection techniques have been implemented on chips but throughput, cost, and multiplexing have not been adequately addressed.

The solid-state DNA interaction detection techniques have also required tagging of target with electrical markers, resulting in possibly altered interactions while requiring sample preparation. The DNA electrical detection techniques mostly employ electrochemical impedance spectroscopy, capillary electrophoresis, or charge perturbation detection using labeled target or labeled probe molecules, surface attached antibodies, and/or with pre-/post-PCR. In label-free detection schemes, the probe DNA is immobilized on the electrodes and impedance is measured in conjunction with or without a reference electrode.

Thus, there is a need for biosensors that overcome these problems. The invention is directed to these, as well as other, important ends.

SUMMARY OF THE INVENTION

The invention provides a nanotechnology-based low-power, rapid, inexpensive, recyclable, and sensitive electrical detection device, system, and method of molecular level concentrations of nucleic acids sequences, including genes, and amino acid sequences with no external sample preparation or labeling or other chemical modification of the sample. The biosensors of the invention may be used in wide variety of applications requiring sensitive nucleic acid and protein detection, including, but not limited to, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

The invention involves a number of preferred features:
1. direct detection of single DNA molecules with no amplification is required;
2. the detection output is purely electrical, i.e., voltage or current signal;
3. ultra-sensitive detection at the molecular level;
4. easy to use and portable; and
5. CMOS-compatible fabrication procedure allows large-scale and inexpensive fabrication of the DNA sensors.

In one embodiment, the invention is directed to devices, comprising:
an electrically-insulating substrate; and
a first detecting unit, comprising:
  a source electrode disposed on said electrically-insulating substrate;
  a drain electrode; and
  a dielectric layer having a substantially uniform thickness and at least one exposed side;
  wherein said dielectric layer is disposed between said source electrode and said drain electrode;
  wherein said dielectric layer is contiguous with said drain electrode;
  wherein said source electrode, said drain electrode and said dielectric layer are self aligned on said at least one exposed side of said dielectric layer;
  a first self-assembling monolayer attached to and in contact with said at least one exposed side of said dielectric layer;
  a second self-assembling monolayer attached to and in contact with said source electrode and said drain electrode;

wherein said second self-assembling monolayer has a polarity different than the polarity of said first self-assembling monolayer; and
at least one capture unit, comprising:
a nanoparticle; and
a plurality of first single-stranded oligonucleotides attached to said nanoparticle;
wherein said first single-stranded oligonucleotides have a first nucleotide sequence complementary to a portion of a first oligonucleotide target; and
wherein said capture unit is located on said exposed side of said dielectric layer and is substantially centered between said source electrode and said drain electrode.

In another embodiment, the invention is directed to devices described herein, further comprising:
a plurality of second detecting units, each second detecting unit comprising:
a source electrode disposed on said electrically-insulating substrate;
a drain electrode; and
a dielectric layer having a substantially uniform thickness and at least one exposed side;
wherein said dielectric layer is disposed between said source electrode and said drain electrode;
wherein said dielectric layer is contiguous with said drain electrode;
wherein said source electrode, said drain electrode and said dielectric layer are self aligned on said at least one exposed side of said dielectric layer;
a first self-assembling monolayer attached to and in contact with said at least one exposed side of said dielectric layer;
a second self-assembling monolayer attached to and in contact with said source electrode and said drain electrode;
wherein said second self-assembling monolayer has a polarity different than the polarity of said first self-assembling monolayer; and
at least one capture unit, comprising:
a nanoparticle; and
a plurality of at least one second single-stranded oligonucleotides attached to said nanoparticle;
wherein said at least one second single-stranded oligonucleotides have a second nucleotide sequence complementary to a portion of a second oligonucleotide target;
wherein said capture unit is located on said exposed side of said dielectric layer and is substantially centered between said source electrode and said drain electrode;
wherein said second nucleotide sequences are the same or different from said first nucleotides sequences in said first detecting unit; and
wherein said second nucleotide sequences are the same or different from other second nucleotide sequences in said plurality of second detecting units.

In further embodiment, the invention is directed to devices described herein, further comprising:
a plurality of microfluidic channels; and
an optional cover.

In further embodiment, the invention is directed to devices, comprising:
an electrically-insulating substrate; and
a first detecting unit, comprising:

a source electrode disposed on said electrically-insulating substrate;
a drain electrode; and
a dielectric layer having a substantially uniform thickness and at least one exposed side;
wherein said dielectric layer is disposed between said source electrode and said drain electrode;
wherein said source electrode, said drain electrode and said dielectric layer are in the same plane;
a first self-assembling monolayer attached to and in contact with said dielectric layer;
a second self-assembling monolayer attached to and in contact with said source electrode and said drain electrode;
wherein said second self-assembling monolayer has a polarity different than the polarity of said first self-assembling monolayer; and
at least one capture unit, comprising:
a nanoparticle; and
a plurality of first single-stranded oligonucleotides attached to said nanoparticle;
wherein said first single-stranded oligonucleotides have a first nucleotide sequence complementary to a portion of a first oligonucleotide target; and
wherein said capture unit is located on said dielectric layer and is substantially centered between said source electrode and said drain electrode.

In yet other embodiment, the invention is directed to systems, comprising:
a device described herein; and
a plurality of nanoparticle reporter conjugates;
wherein said nanoparticle reporter conjugates comprise at least one nanoparticle and a single-stranded oligonucleotide complementary to at least a portion of said first oligonucleotide target different than said portion complementary to said first nucleotide sequence; and
wherein said nanoparticle is a metal, semiconductor, or magnetic colloidal particle.

In yet another embodiment, the invention is directed to systems, comprising:
a multiplexing device described herein; and
a plurality of first nanoparticle reporter conjugates; and
a plurality of at least one second nanoparticle reporter conjugates;
wherein said first nanoparticle reporter conjugates comprise at least one nanoparticle and a single-stranded oligonucleotide complementary to at least a portion of said first oligonucleotide target different than said portion complementary to said first nucleotide sequence;
wherein said nanoparticle in said first nanoparticle reporter conjugate is a metal, semiconductor, or magnetic colloidal particle;
wherein said at least one second nanoparticle reporter conjugates comprise at least one nanoparticle and a single-stranded oligonucleotide complementary to at least a portion of said at least one second oligonucleotide target different than said portion complementary to said at least one second nucleotide sequence;
wherein said nanoparticle in said at least one second nanoparticle reporter conjugate is a metal, semiconductor, or magnetic colloidal particle;
wherein said second nanoparticle reporter conjugates are the same or different from said first nanoparticle reporter conjugates; and
wherein said second nanoparticle reporter conjugates are the same or different from said other second nanoparticle reporter conjugates.

In other embodiments, the invention is directed to systems, further comprising:
  an electrical reading device for interrogating said device described herein.

In one embodiment, the invention is directed to methods for detecting nucleic acid hybridization, comprising:
  providing a device described herein;
  passivating said first self-assembling monolayer;
  providing a solution comprising at least one buffer and single-stranded oligonucleotide target under hybridizing conditions;
    wherein said single-stranded oligonucleotide target hybridizes a portion of said first nucleotide sequence thereby leaving an unhybridized portion of said single-stranded oligonucleotide target;
  providing a plurality of first nanoparticle reporter conjugates under hybridizing conditions;
    wherein said first nanoparticle reporter conjugates comprise at least one nanoparticle and an oligonucleotide complementary to said unhybridized portion of said single-stranded oligonucleotide target;
    wherein said nanoparticle in said first nanoparticle reporter conjugate is a metal, semiconductor, or magnetic colloidal particle; applying a voltage drop across said electrodes; and
  measuring a change in conductivity, resistivity, capacitance, or impedance across said electrodes at known locations to determine perfect complementarity of said oligonucleotide target to said first oligonucleotide sequence.

In yet other embodiment, the invention is directed to methods further comprising:
  washing to remove unhybridized components from said detecting unit.

In another embodiment, the invention is directed to methods further comprising:
  heating said device to remove said hybridized targets and said hybridized nanoparticle reporter conjugates from said probe to permit recycling of said detecting unit.

In still further embodiments, the invention is directed to methods further comprising:
  heating a solution comprising double stranded oligonucleotide target to form said solution comprising single-stranded oligonucleotide target.

In a further embodiment, the invention is directed to methods further comprising:
  forming a temperature gradient to focus said single stranded oligonucleotide target at said detecting unit.

In one embodiment, the invention is directed to methods further comprising:
  applying an electric field to direct said single-stranded oligonucleotide target to said capture unit to reduce hybridization time.

In another embodiment, the invention is directed to methods further comprising:
  providing a multiplexing device described herein;
  passivating said first self-assembling monolayer;
  providing a solution comprising at least one buffer and single-stranded oligonucleotide target under hybridizing conditions;
    wherein said single-stranded oligonucleotide target hybridizes a portion of said at least one second nucleotide sequence thereby leaving an unhybridized portion of said single-stranded oligonucleotide target;
  providing a plurality of at least one second nanoparticle reporter conjugates under hybridizing conditions;
    wherein said second nanoparticle reporter conjugates comprise at least one nanoparticle and an oligonucleotide complementary to said unhybridized portion of said single-stranded oligonucleotide target;
    wherein said nanoparticle in said second nanoparticle reporter conjugate is a metal, semiconductor, or magnetic colloidal particle;
    wherein said second nanoparticle reporter conjugates are the same or different from said first nanoparticle reporter conjugates;
    wherein said second nanoparticle reporter conjugates are the same or different from said other second nanoparticle reporter conjugates;
  wherein said measuring step is carried out in parallel or sequentially for said first detecting unit and said plurality of said additional detecting units.

In another embodiment, the invention is directed to processes for preparing a nano-scale bridging biosensor, comprising:
  forming a device, comprising:
    an electrically-insulating substrate; and
    a first detecting unit, comprising:
      a source electrode disposed on said electrically-insulating substrate;
      a drain electrode; and
      a dielectric layer having a substantially uniform thickness and at least one exposed side;
      a first self-assembling monolayer attached to and in contact with said at least one exposed side of said dielectric layer;
      a second self-assembling monolayer attached to and in contact with said source electrode and said drain electrode;
      wherein said second self-assembling monolayer has a polarity different than the polarity of said first self-assembling monolayer;
      wherein said dielectric layer is disposed between said source electrode and said drain electrode;
      wherein said dielectric layer is contiguous with said drain electrode; and
      wherein said source electrode, said drain electrode and said dielectric layer are self aligned on said at least one exposed side of said dielectric layer;
    providing on said exposed side of said dielectric layer and substantially centered between said source electrode and said drain electrode at least one capture unit, said capture unit comprising:
      a nanoparticle; and
      a plurality of first single-stranded oligonucleotides attached to said nanoparticle; and
      wherein said first single-stranded oligonucleotides have a first nucleotide sequence complementary to a portion of a first oligonucleotide target; and
    passivating said first self-assembling monolayer.

In yet other embodiments, the invention is directed to devices, comprising:
  an electrically-insulating substrate; and
  a first detecting unit, comprising:
    a source electrode disposed on said electrically-insulating substrate;
    a drain electrode; and
    a dielectric layer having a substantially uniform thickness and at least one exposed side;
    wherein said dielectric layer is disposed between said source electrode and said drain electrode;
    wherein said dielectric layer is contiguous with said drain electrode;

wherein said source electrode, said drain electrode and said dielectric layer are self aligned on said at least one exposed side of said dielectric layer;

a first self-assembling monolayer attached to and in contact with said at least one exposed side of said dielectric layer;

a second self-assembling monolayer attached to and in contact with said source electrode and said drain electrode;

wherein said second self-assembling monolayer has a polarity different than the polarity of said first self-assembling monolayer; and at least one capture unit, comprising:
  a nanoparticle; and
  a plurality of first antibodies attached to said nanoparticle;
  wherein said first antibody have affinity to a portion of a first polypeptide target; and
  wherein said capture unit is located on said exposed side of said dielectric layer and is substantially centered between said source electrode and said drain electrode.

In one embodiment, the invention is directed to methods for detecting protein-antibody interaction, comprising:

providing a device described herein;
passivating said first self-assembling monolayer;
providing a solution comprising at least one buffer and polypeptide target under binding conditions;
  wherein a portion of said polypeptide target binds said first antibody;
providing a plurality of first nanoparticle reporter conjugates under hybridizing conditions;
  wherein said first nanoparticle reporter conjugates comprise at least one nanoparticle and a second antibody capable of binding the unbound portion of said polypeptide target;
  wherein said nanoparticle in said first nanoparticle reporter conjugate is a metal, semiconductor, or magnetic colloidal particle; applying a voltage drop across said electrodes; and
measuring a change in conductivity, resistivity, capacitance, or impedance across said electrodes at known locations to determine perfect binding of said polypeptide target to said first antibody.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

(a)-(b) The schematic of the electrostatic funneling concept. The electrostatic guiding structure is made by functionalizing the substrate surface with self-assembled monolayers (SAMs) having alternating polarities.
(c) An SEM image demonstrating the effectiveness of the electrostatic funneling. Bright dots: ~20 nm Au nanoparticles (AuNPs); Dark lines and bright lines are silicon oxide and gold surfaces, respectively. The placement precision (average deviation of NP positions from the center of the silicon oxide line) was measured to be ~6 nm.

Figure 4:
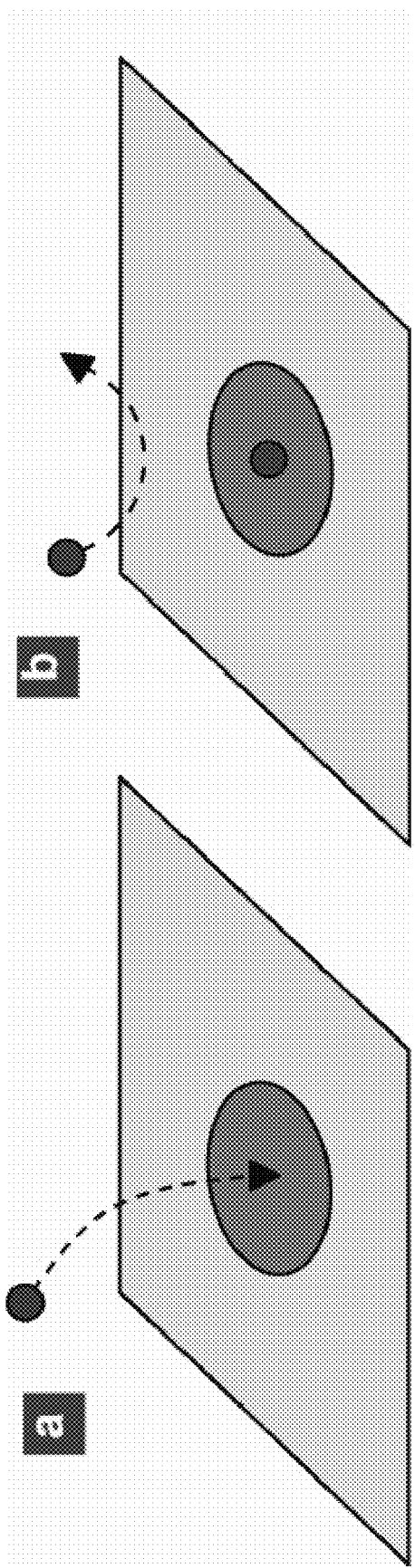

FIG. 4 illustrates the concept of single-particle placement (SPP):
(a) A nanoparticle in a colloid is electrostatically guided onto a circle center.
(b) Once a nanoparticle occupies a circle, the approach of other nanoparticles is prohibited. Inside the circle: positively charged; outside the circle: negatively charged; and nanoparticle: negatively charged.

Figure 5:
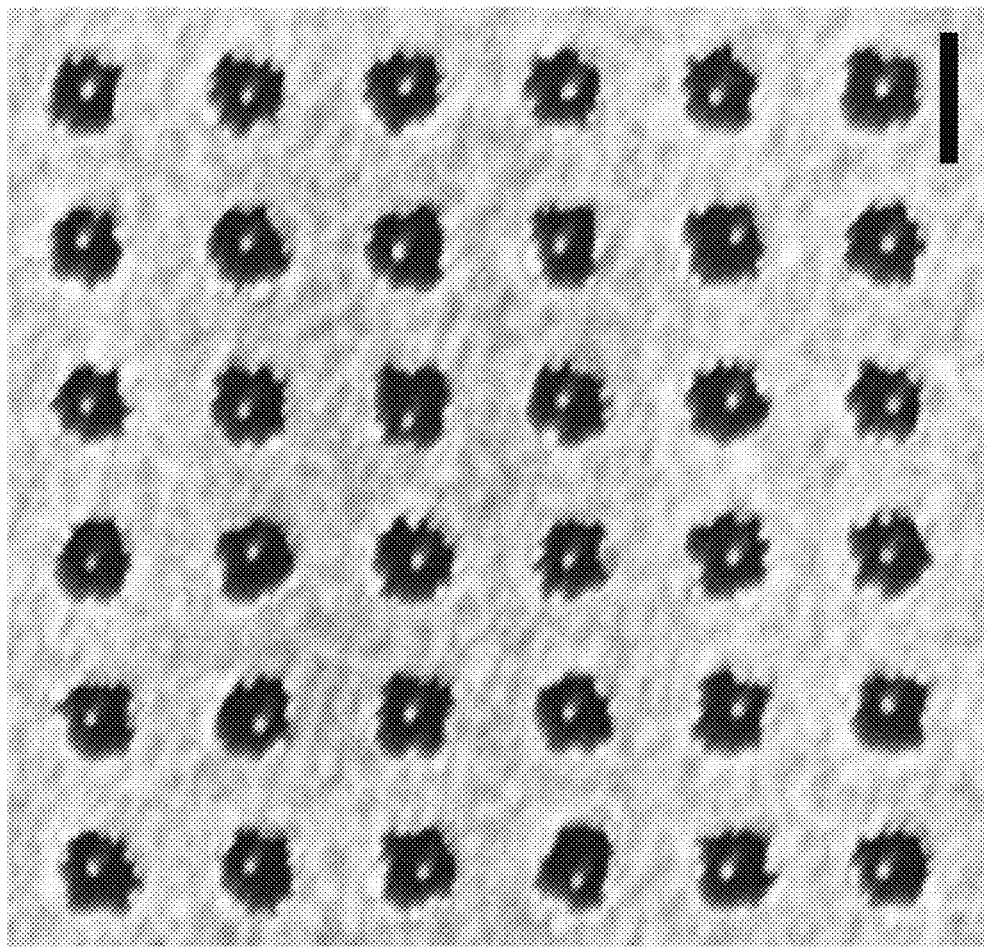

FIG. 5 is a scanning electron micrograph (SEM) image demonstrating the SPP.3 Bright dots: ~20 nm AuNPs; dark circular patterns: silicon oxide; bright area: Au surface. Scale bar: 200 nm.

Figure 6:
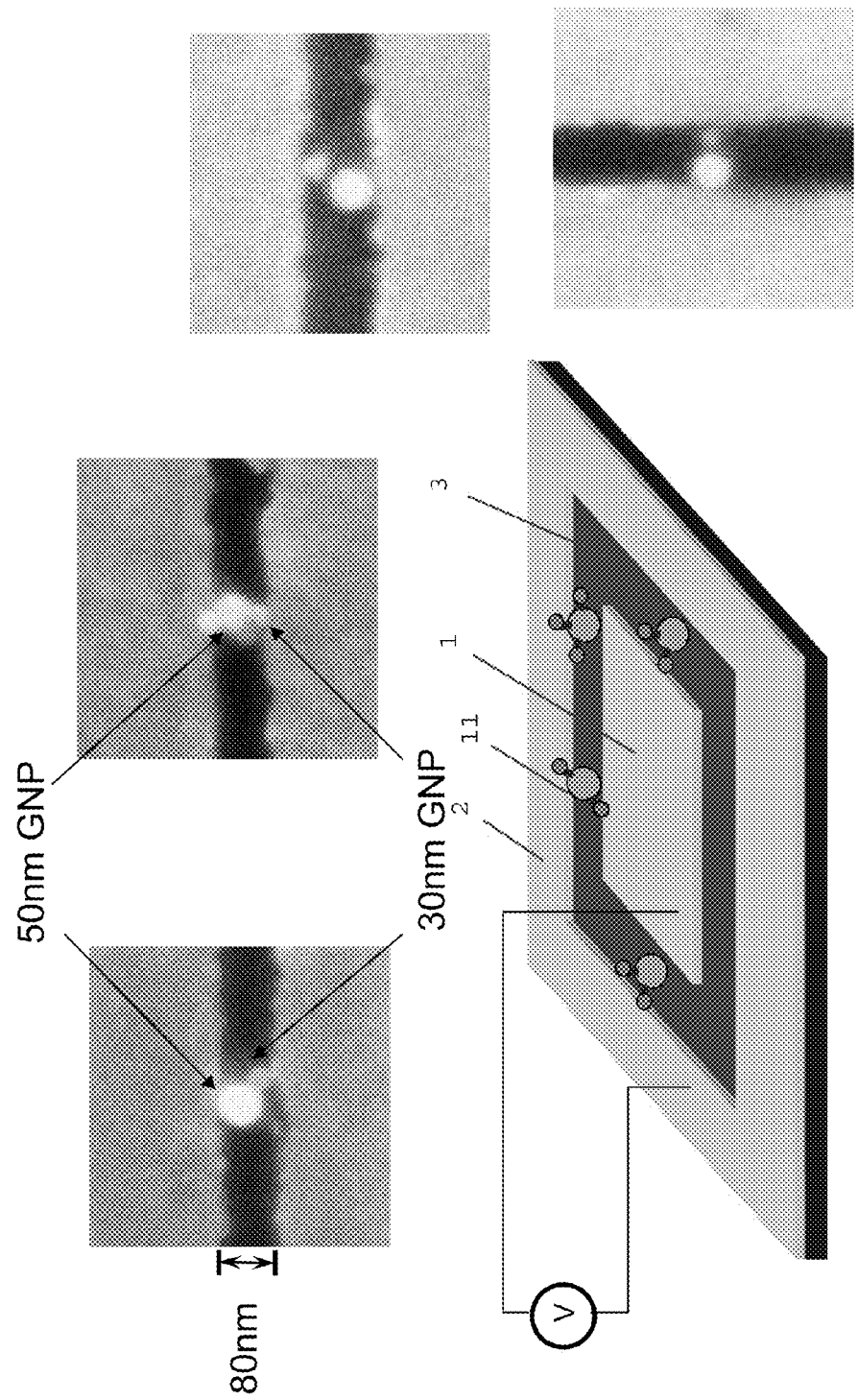

FIG. 6 shows a schematic diagram and scanning electron micrograph (SEM) images of one embodiment of the device of the invention (with planar design), when exposed to target DNA with perfect complementarity to the single-stranded oligonucleotide of the capture unit, showing the formation of nanoparticle satellites.

Figure 7:
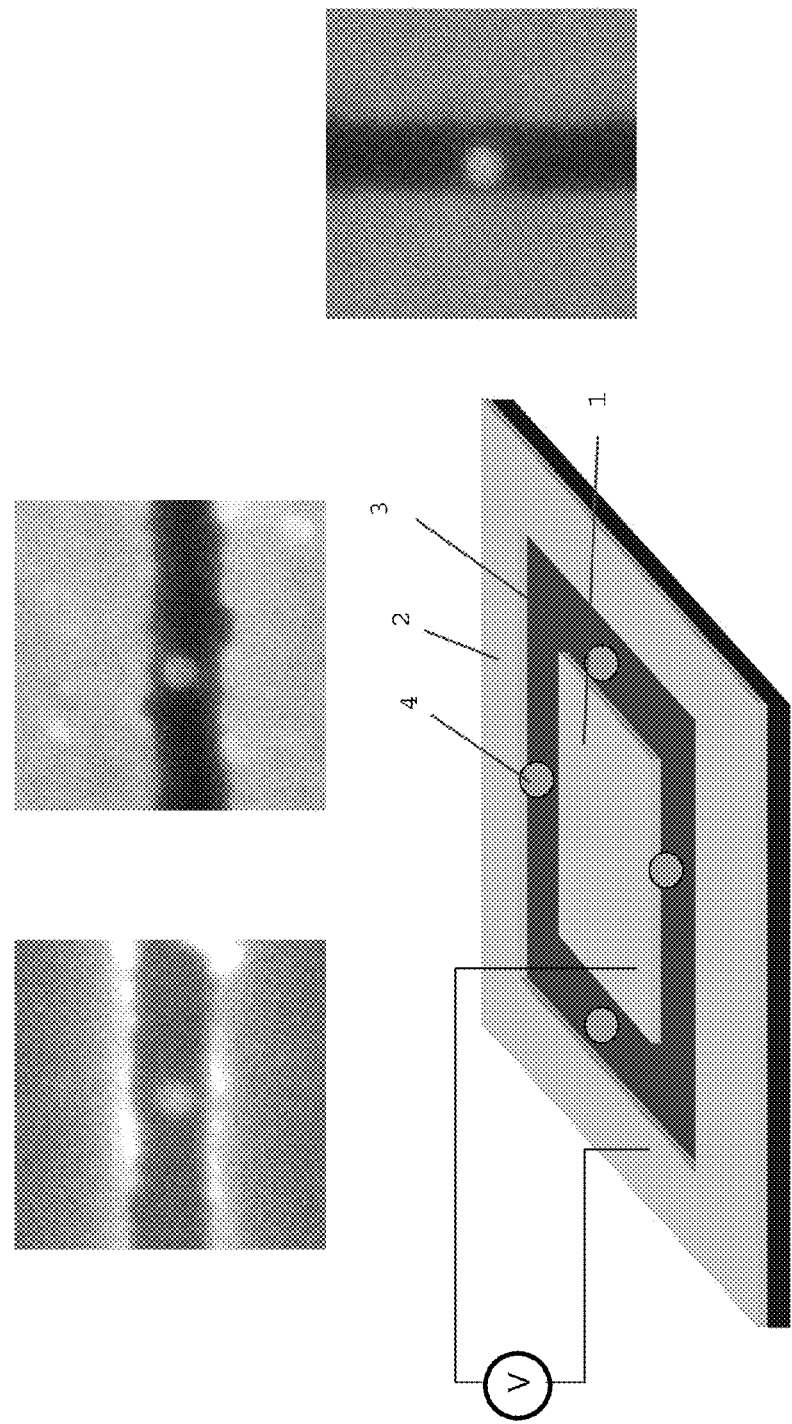

FIG. 7 shows a schematic diagram and scanning electron micrograph (SEM) images of a control device (with planar design), when exposed to target DNA lacking perfect complementarity (mismatched; control) to the single-stranded oligonucleotide of the capture unit, showing the lack of formation of nanoparticle satellites.

Figure 8:
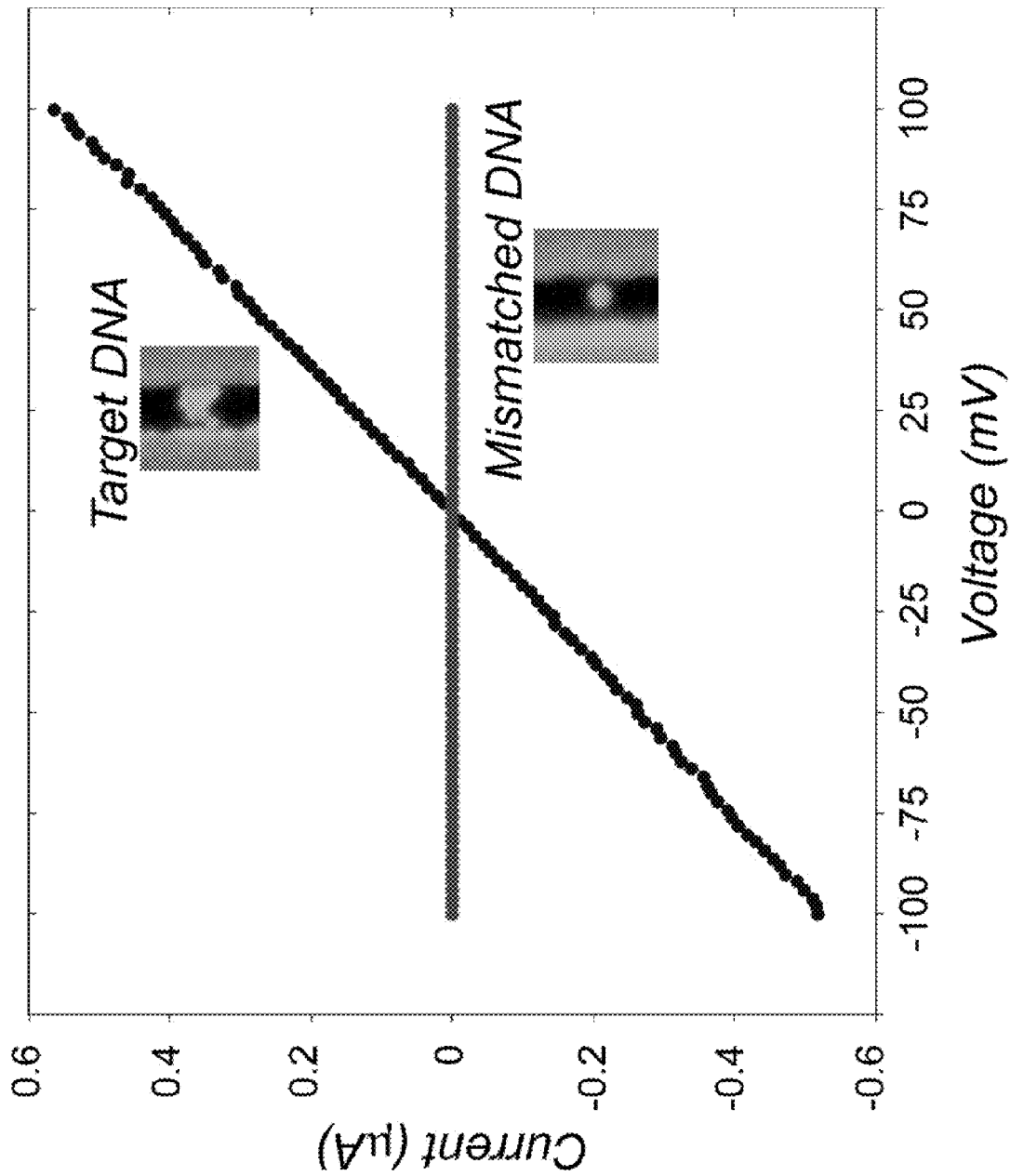

FIG. 8 is an I-V plot of current (in µA) as a function of applied voltage (in mV) for target DNA with perfect complementarity to the single-stranded oligonucleotide of the capture unit and for target DNA lacking perfect complementarity (mismatched; control) to the single-stranded olignonucleotide of the capture unit, establishing the ability to detect the perfect complementarity electrically.

Figure 9:
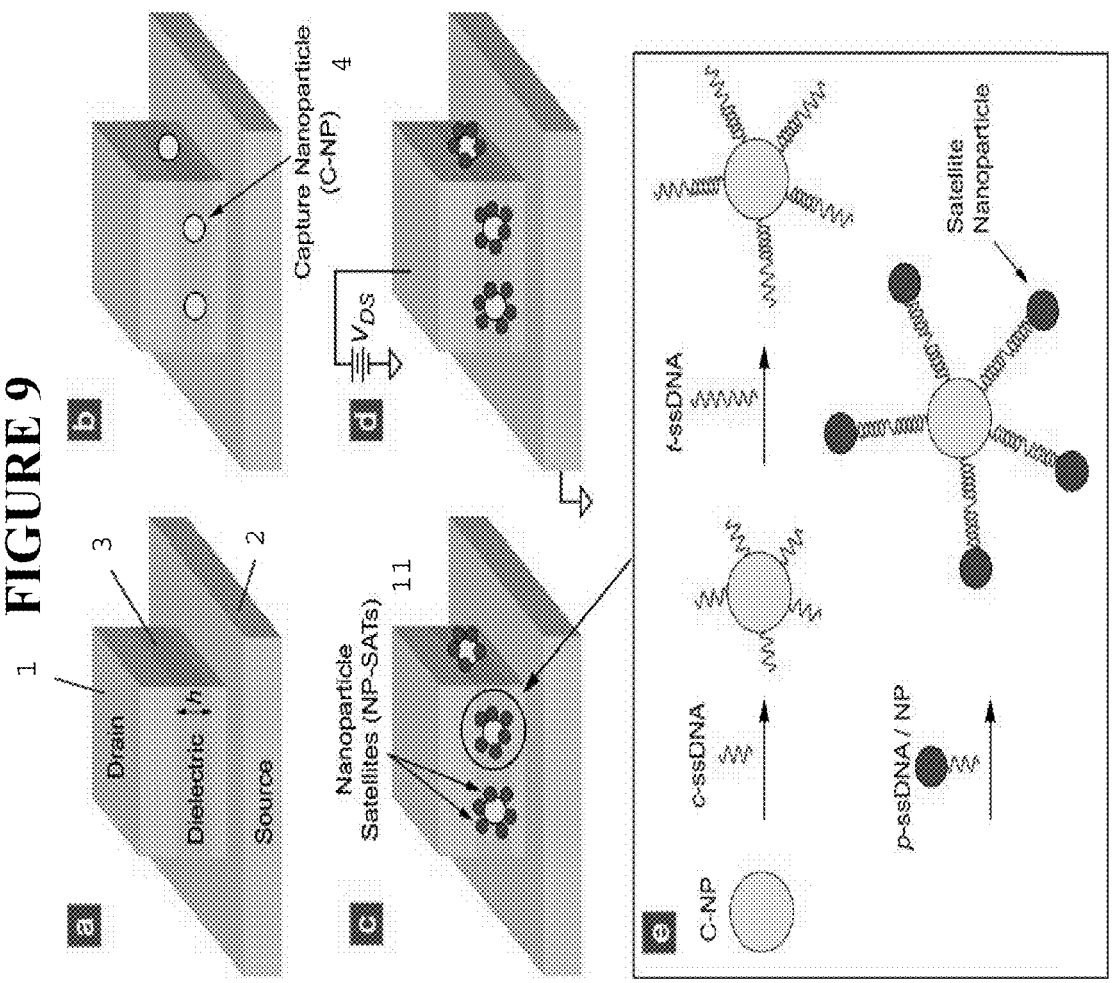

FIG. 9 is a schematic of one embodiment of the nanoparticle-bridge DNA sensor:
(a) Formation of vertically self-aligned drain/dielectric/source structure. The source/drain gap h can be controlled with nanoscale precision.
(b) Precise placement of capture nanoparticles (C-NPs) on the center positions of the electrode gap.
(c) Formation of nanoparticle satellites (NP-SATs) around C-NPs through DNA hybridizations.
(d) I-V measurement. The NP-SATs/C-NP conjugates act as current bridges that connect the two electrodes electrically.
(e) Schematic for the formation of NP-SATs/C-NP conjugate via DNA hybridizations. Schematic is not to scale (the sizes of DNA are exaggerated).

Figure 10:
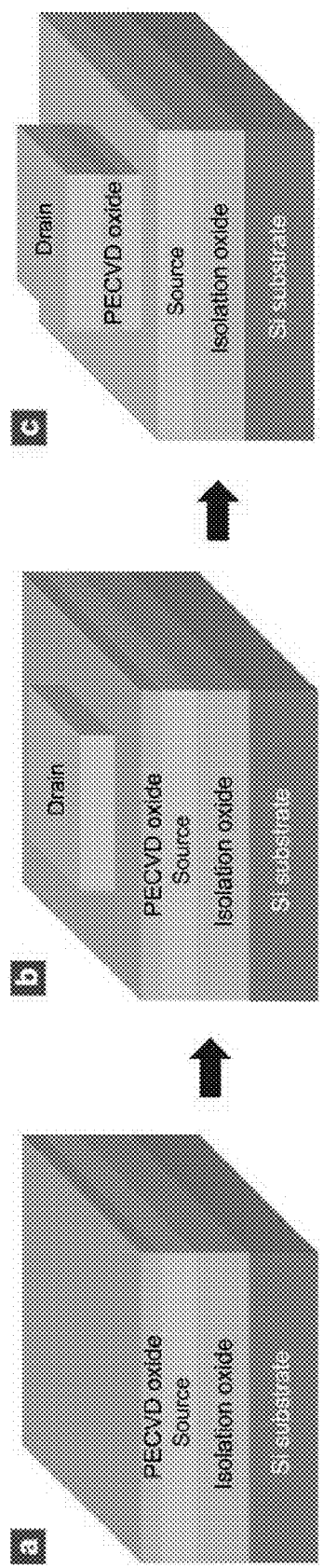

FIG. 10 shows the formation of self-aligned drain/dielectric/source structure:
(a) Formation of a film stack using oxidation, metal evaporation, and deposition of PECVD oxide.
(b) Formation of drain electrode with photolithography, deposition of drain electrode, and lift-off.
(c) Formation of a self-aligned drain/dielectric/source stack using reactive ion etching (RIE). Drain electrode is used as a hard mask.

Figure 11:
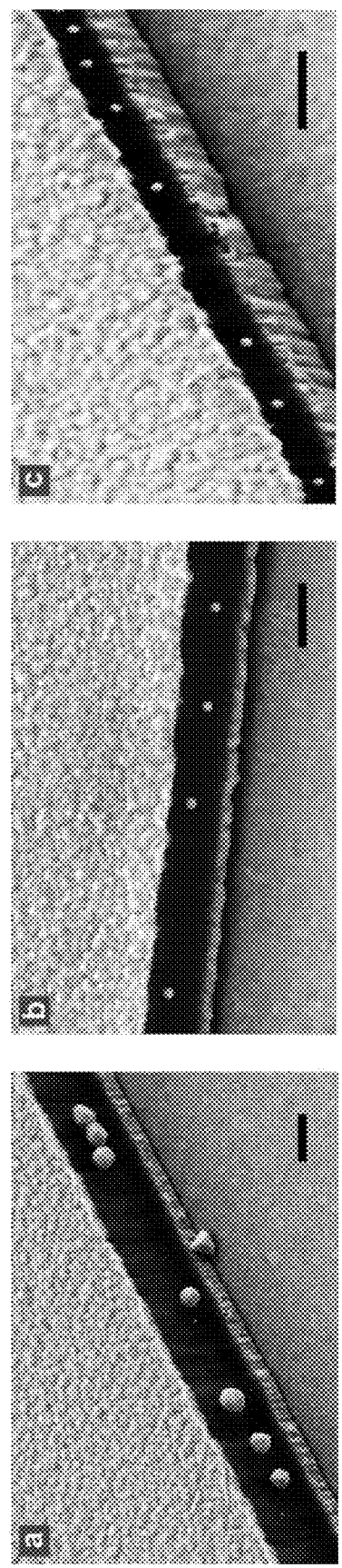

FIG. 11 shows nanoparticle placement in 3-dimensional step structure. Nanoparticles were placed along the center locations of the exposed sidewall. Bright dots are Au NPs with diameters of ~200, ~80, and ~50 nm for (a), (b), and (c), respectively. Scale bars: 400 nm.

Figure 12:
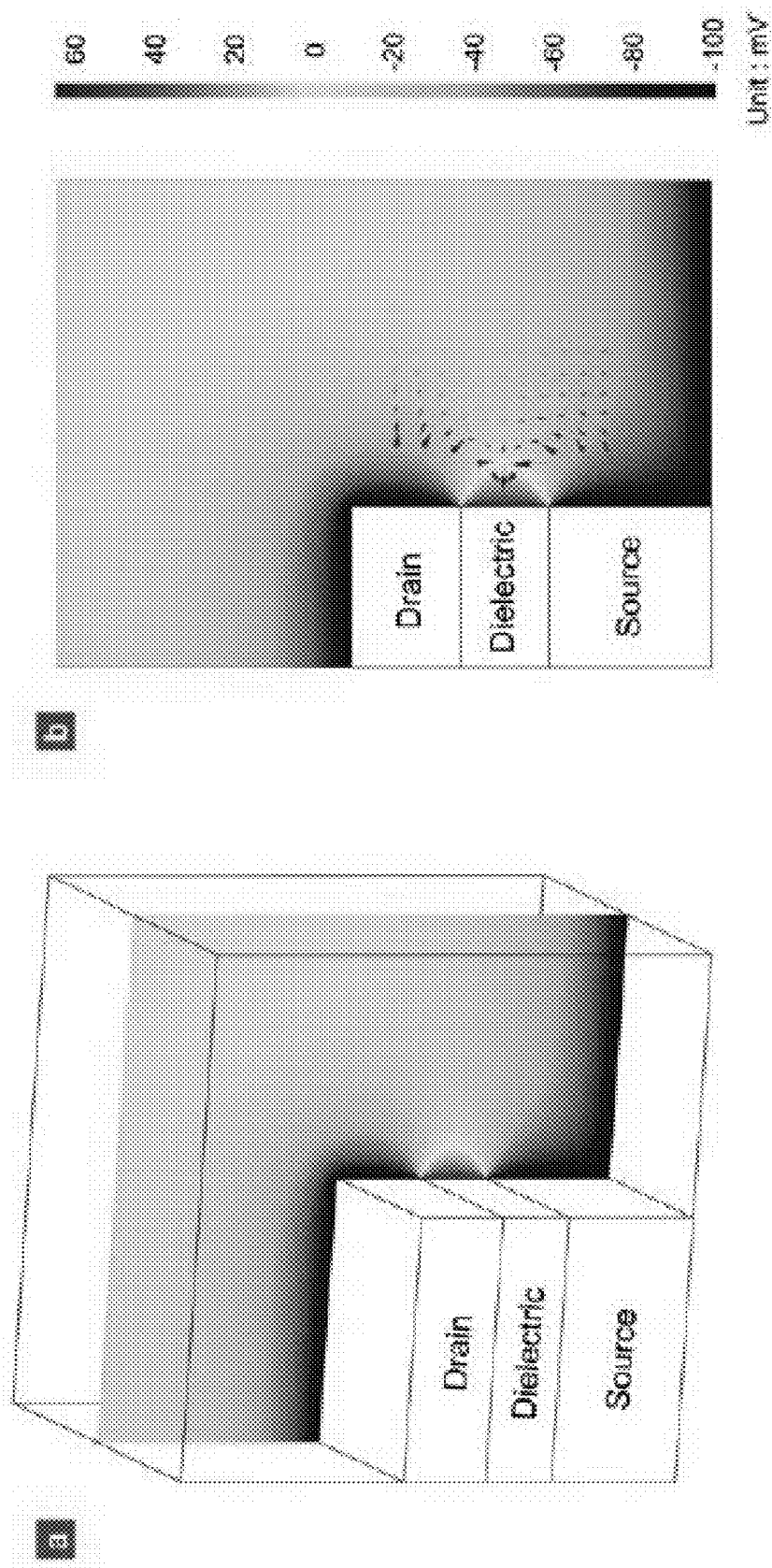

FIG. 12:
(a) Calculated electrostatic potential for a drain/dielectric/source stack geometry.
(b) Magnified cross sectional view of the region near the oxide sidewall. Arrows display electrostatic fields.

Figure 13:
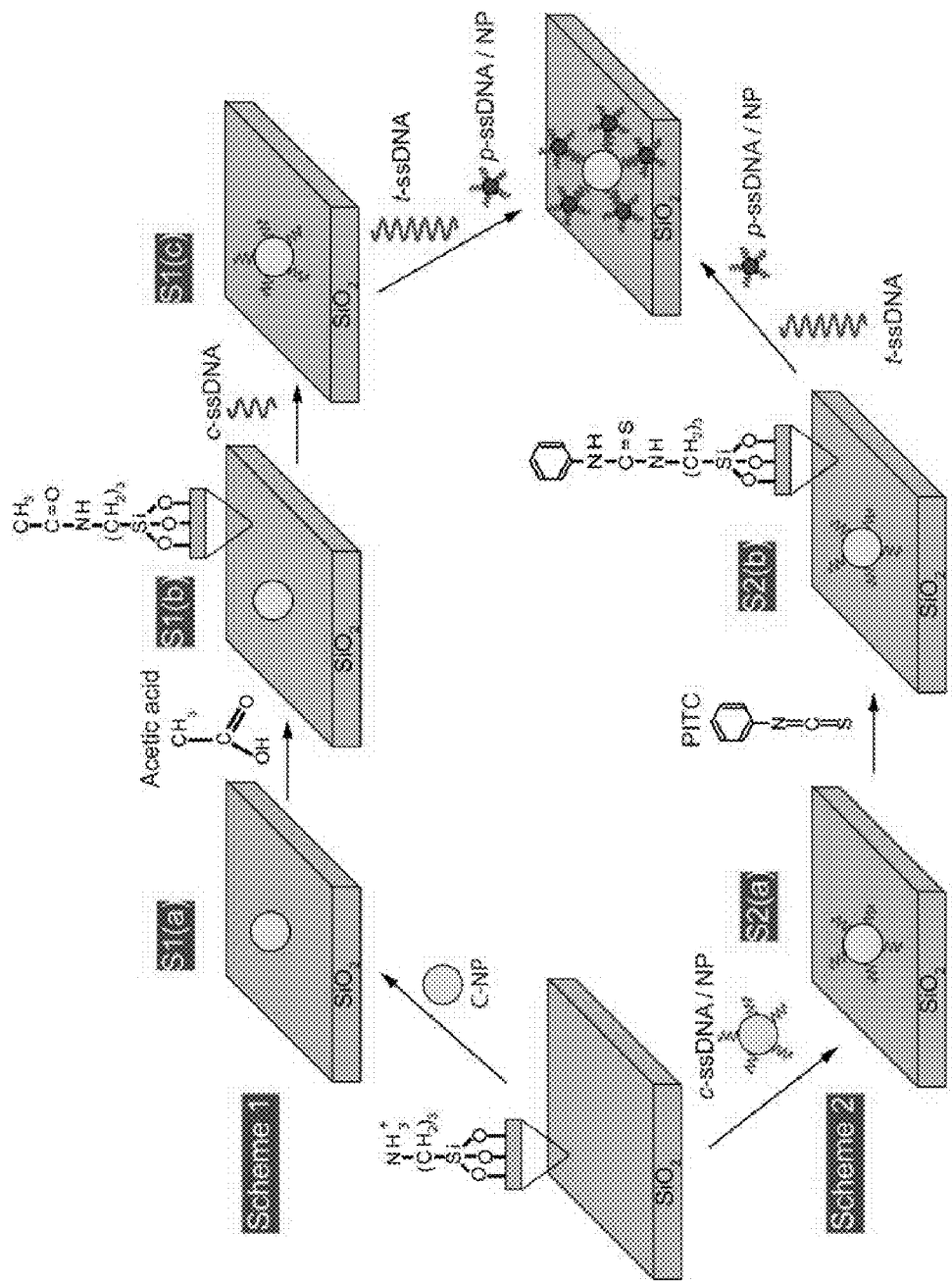

FIG. 13 shows surface passivation for exclusive DNA hybridization on C-NP. Top: Scheme 1; passivation with methyl group. Bottom: Scheme 2; passivation with benzene group.

Figure 14:
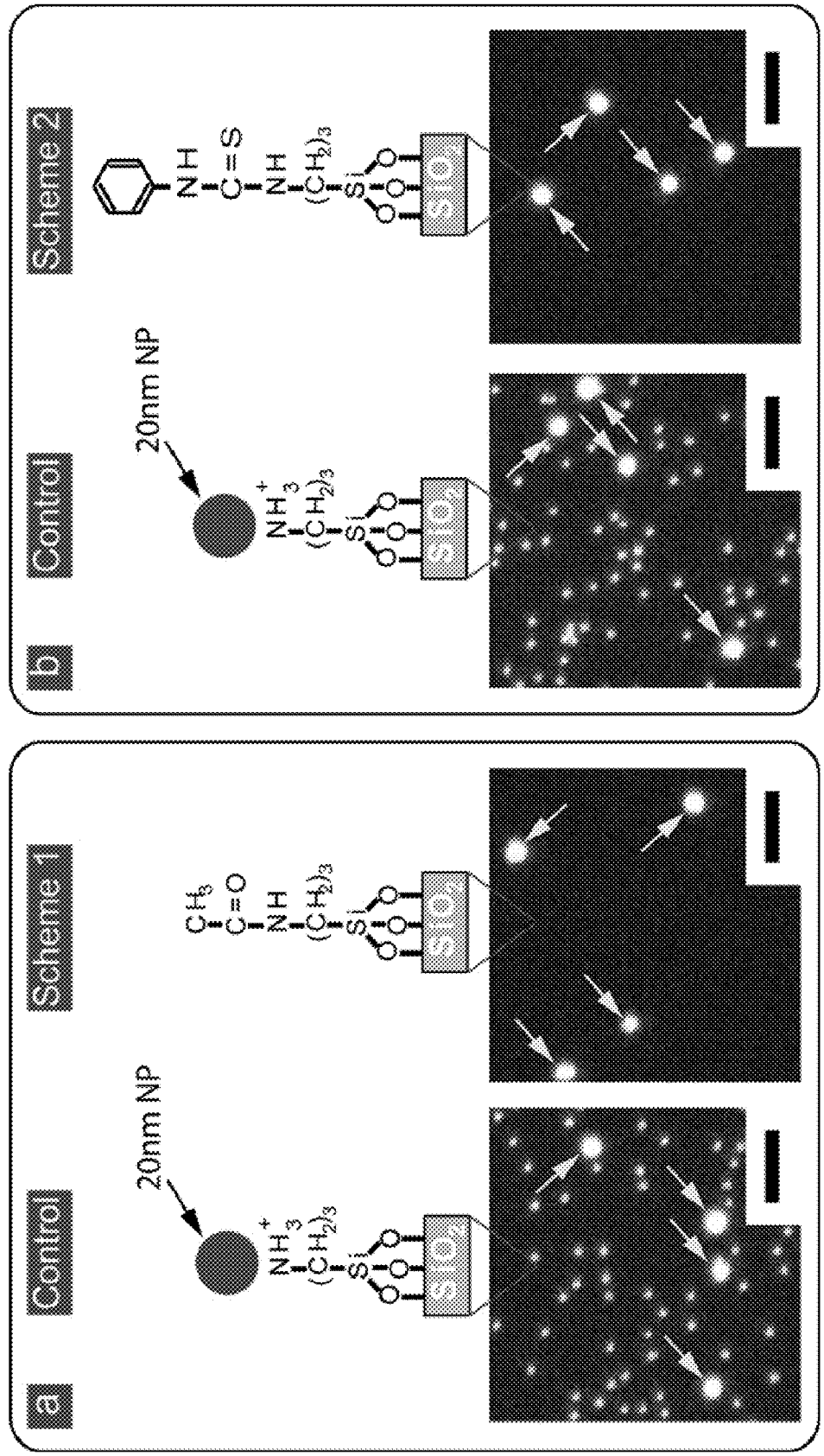

FIG. 14 demonstrates surface passivation on blanket wafers.
(a) Using Scheme 1.
(b) Using Scheme 2. The arrows indicate ~50 nm AuNPs (C-NPs). Small bright dots are ~20 nm AuNPs. Scale bars: 200 nm.

Figure 15:
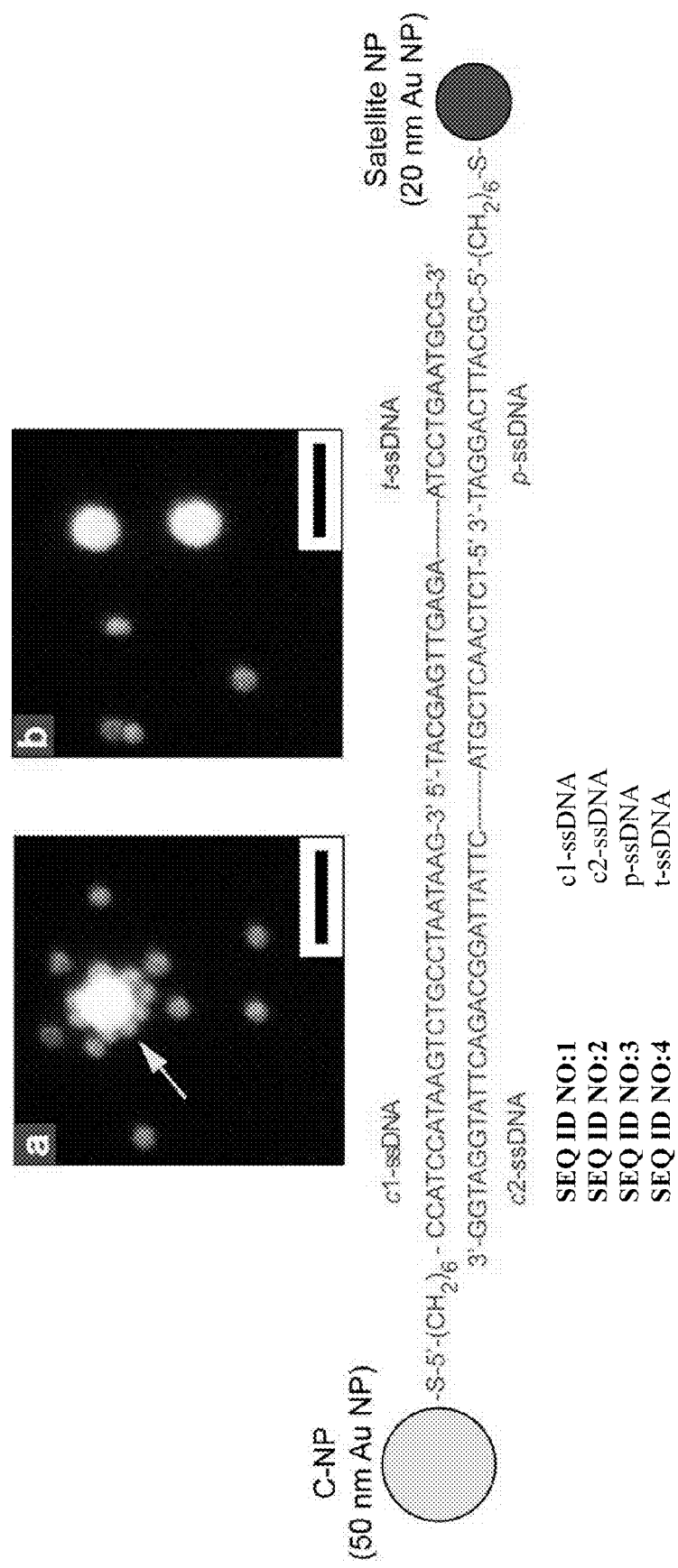

FIG. 15 shows the formation of NP-SATs around C-NPs via DNA hybridization in a solution phase:
(a) SEM image of NP-SATs formed on a C-NP (arrow).
(b) SEM image for a control sample which had no exposure to t-ssDNA. Bottom: DNA sequences for c-ssDNA (c1-ss-DNA+c2-ssDNA), t-ssDNA, and p-ssDNA. Scale bars: 100 nm.

Figure 16:
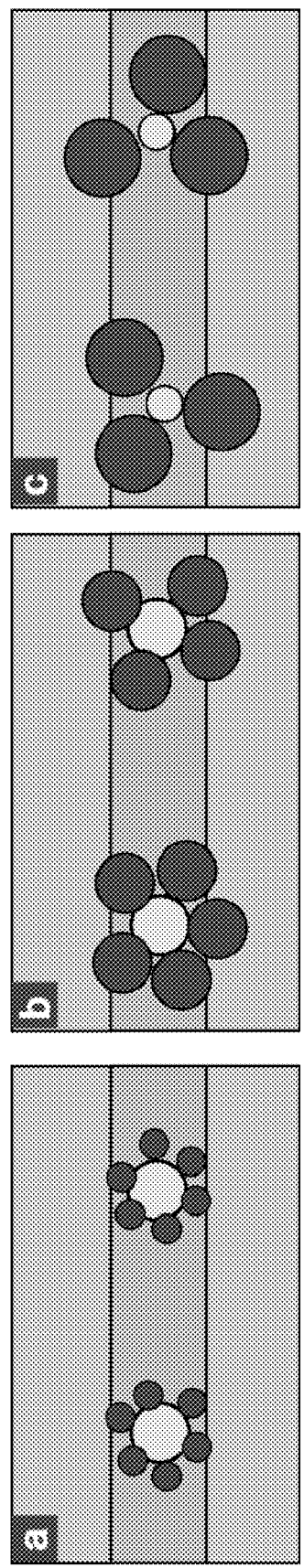

FIG. 16 shows the formation of NP-SATs/C-NPs with varying NP sizes.
(a) C-NPs are larger than satellite NPs.
(b) C-NPs and satellite NPs are comparable in size.
(c) C-NPs are smaller than satellite NPs.

Figure 17:
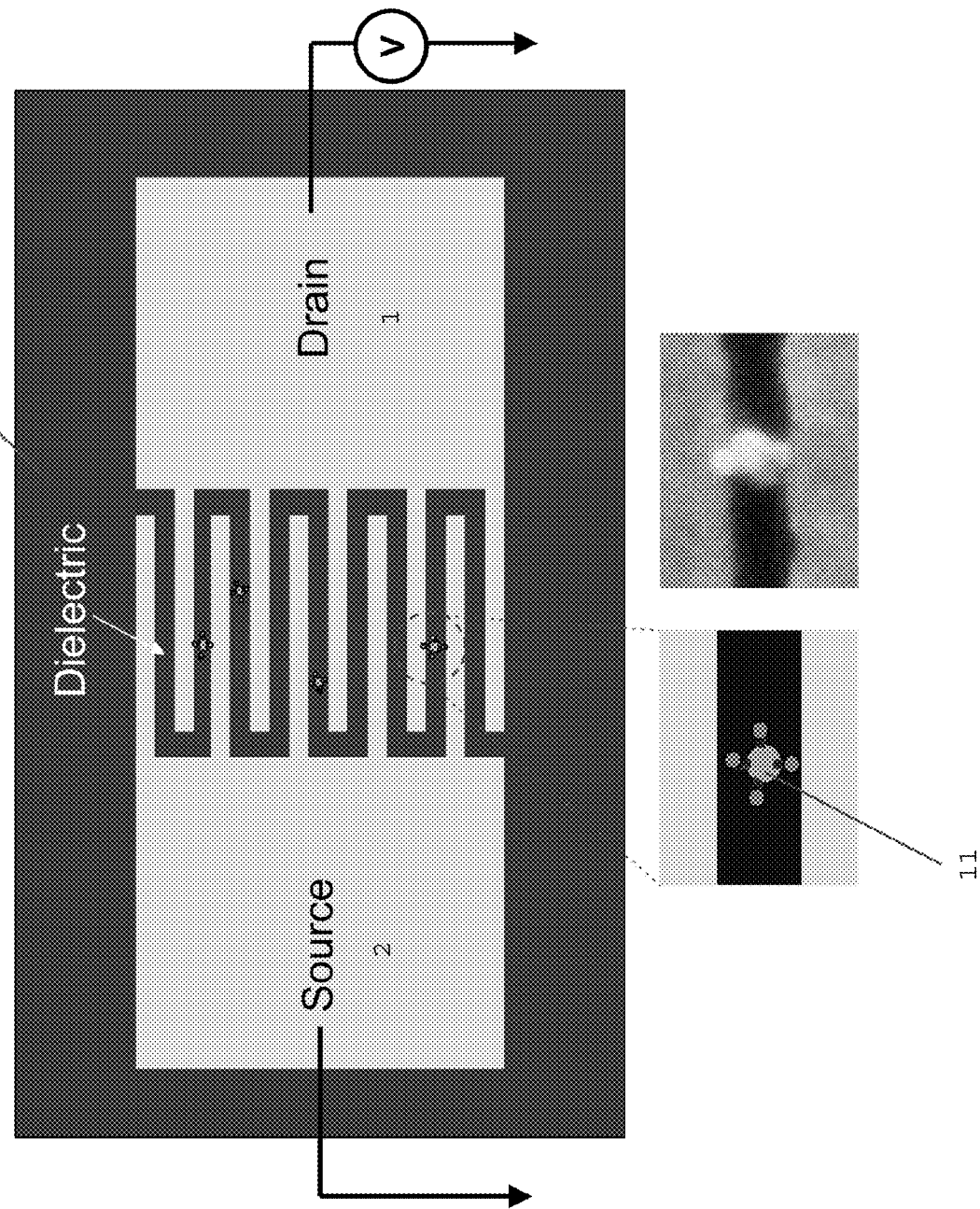

FIG. 17 is a schematic diagram of an alternate embodiment of the device of the invention with a planar design in which the source and drain electrodes are separated by dielectric material, including an exploded view of the capture unit with satellite nanoparticles and a photograph of the same.

DETAILED DESCRIPTION OF THE INVENTION

The invention provides devices, systems, and methods for detecting nucleic acid hybridization, including single nucleic base mutations, are disclosed using capture units having nanoparticles with attached single-stranded oligonucleotides that is capable of hybridizing target oligonucleotides and reporter molecules having nanoparticles with attached single-stranded oligonucleotides, without the use of labeling or target modification.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Unless defined otherwise, all technical and scientific terms used herein have the same meaning as commonly understood to one of ordinary skill in the art to which this invention belongs. The following definitions are provided for the full understanding of terms used in this specification.

As used herein, the article "a," "an," and "the" means "at least one," unless the context in which the article is used clearly indicates otherwise.

As used herein, the term "nucleic acid" as used herein means a polymer composed of nucleotides, e.g. deoxyribonucleotides or ribonucleotides.

As used herein, the terms "ribonucleic acid" and "RNA" as used herein mean a polymer composed of ribonucleotides.

As used herein, the terms "deoxyribonucleic acid" and "DNA" as used herein mean a polymer composed of deoxyribonucleotides.

As used herein, the term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™. technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

As used herein, the term "polynucleotide" refers to a single or double stranded polymer composed of nucleotide monomers of generally greater than 100 nucleotides in length and up to about 8,000 or more nucleotides in length.

As used herein, "polypeptide" refers to a compound made up of a single chain of D- or L-amino acids or a mixture of D- and L-amino acids joined by peptide bonds. Generally, peptides are about 2 to about 50 amino acids in length.

As used herein, the term "array" means a substrate having a plurality of binding agents (probes) stably attached to its surface, where the binding agents (probes) are arranged in a spatially defined and physically addressable manner across the surface of the substrate in any of a number of different patterns. Generally, at least two of the plurality of binding agents (probes) are different.

As used herein, the term "complementary" refers to the topological compatibility or matching together of interacting surfaces of a probe molecule and its target. Thus, the target and its probe can be described as complementary, and furthermore, the contact surface characteristics are complementary to each other.

As used herein, the term "hybridization" refers to a process of establishing a non-covalent, sequence-specific interaction between two or more complementary strands of nucleic acids into a single hybrid, which in the case of two strands is referred to as a duplex.

As used herein, the term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

As used herein, the term "melting" refers to the denaturation of a double-stranded nucleic acid sequence due to high temperatures, resulting in the separation of the double strand into two single strands by breaking the hydrogen bonds between the strands.

As used herein, the term "capture" refers to the ability of an immobilized molecule to be recognized by a particular target. The immobilized molecules, such a single stranded oligonucleotide, is referred to as a "capture probe."

As used herein, the term "target" refers to a molecule that has an affinity for a given probe. Targets may be naturallyoccurring or man-made molecules. Also, they can be employed in their unaltered state or as aggregates with other species.

As used herein, the term "biological chip," "chip", or "biosensor" refers to a substrate having a surface to which one or more arrays of probes is attached.

As used herein, the term "wafer" refers to a substrate having a surface to which a plurality of probe arrays are attached. On a wafer, the arrays are physically separated by a distance of at least about a millimeter, so that individual chips can be made by dicing a wafer or otherwise physically separating the array into units having a probe array.

As used herein, the phrase "two perfectly complementary nucleotide sequences" refers to a nucleic acid duplex wherein the two nucleotide strands match according to the Watson-Crick base pair principle, i.e., A-T and C-G pairs in DNA:DNA duplex and A-U and C-G pairs in DNA:RNA or RNA:RNA duplex, and there is no deletion or addition in each of the two strands.

As used herein, the phrase "substantially uniform thickness" with reference to the dielectric layer of the invention refers to a dimension that varies by less than about 20%, preferably less than about 10%, and more preferably less than about 5%, over the area covered by the layer.

As used herein, the phrase "substantially centered between" is used with reference to the capture unit of the invention and means that the location of the midpoint of the nanoparticle in no more than about 20%, preferably less than about 10%, and more preferably less than about 5%, away from the midpoint between the source and drain electrodes.

As used herein, the term "self-aligned," when used in reference to the source electrode, drain electrode, and dielectric layer, means that the shape of the drain is transferred to dielectric layer and source electrode, and that the drain/dielectric/source stack is aligned, and that exposed side is substantially planar (varies by less than about 20%, preferably less than about 10%, and more preferably less than about 5%) with respect to shapes having straight sides (and smooth for shapes having curved sides).

As used herein, the term "dielectric" refers to an electrical insulating material that may be polarized by the action of an applied electric field. When a dielectric material is placed in electric field, electric charges do not flow through the material, as in conductor, but only slightly shift from their average equilibrium positions causing dielectric polarization: positive charges are displaced along the field and negative charges shift in the opposite direction. This creates an internal electric field which partly compensates the external field inside the dielectric material.

As used herein, the term "portion" with reference an oligonucleotide, refers to less than the entire sequence of nucleic acid bases forming the oligonucleotide (when used in reference to an oligonucleotide) or less than entire sequence of peptides forming the polypeptide (when used in reference to a polypeptide). If a portion of oligonucleotide target hybridizes (due to perfect complementarity) with the single-stranded oligonucleotide (or single-stranded portion of a oligonucleotide) in the capture unit, then the remaining portion of the oligonucleotide target will be available to hybridize with the nanoparticle reporter conjugates. If a portion of a polypeptide target binds (due to binding specificity) with a first antibody in the capture unit, then the remaining portion of the polypeptide target will be available to specifically bind with the nanoparticle reporter conjugates.

As used herein, the term "nanoparticle" refers to any nanoscale object or entity, including, but not limited to tube, rod, hollow sphere, solid sphere, and like. Nanoparticles are not required to be spherical in shape.

To more fully understand the invention, the various embodiments will be described more fully and with respect to the figures.

The nano-scale bridge biosensor devices of the invention may utilize a single electron structure architecture, which is known in the art, and is described in U.S. Pat. No. 7,465,953, Ray, V., et al., *Nature Nanotechnology*, Volume 3, October 2008; and Ma, L.-C., et al., Electrostatic funneling for precise nanoparticle placement: A route to wafer-scale integration. *Nano Lett.* 7, 439-445 (2007), each of which are incorporated by reference in their entirety. In general, fabrication of the single electron structure includes the following parameters: (a) the distance between source and drain electrodes are controlled and on a nanometer scale; (b) the distance between source and drain electrodes depends on the size of one or more capture units (akin to the charging islands or Coulomb island) and the thickness of one or more tunneling barriers (e.g., the dielectric layer); (c) the capture unit must be precisely positioned between source and drain electrodes to allow direct contact via the electrodes or electron tunneling via the charging island. Nanoscale dimensions are possible using deposition and/or oxidation technology as known to one of ordinary skill in the art. These technologies allow the thickness of the dielectric layers to be controlled to within a few angstroms. By controlling the thickness of these layers at nanoscale or sub-nanoscale dimensions, the present invention achieves precise control in defining the distance between the source and drain. The present invention does not have to rely on controlling the lateral dimension at a nanoscale level. The dielectric layer is typically a dielectric that acts as a tunneling barrier between drain and charging island. The exposed sidewall of the dielectric layer serves as a surface on which an additional component, a self-assembled monolayer (SAM) structure, when provided, may come in contact with, bind to and/or attach.

The single electron transistor structure is capable of contacting at least one nanoparticle (as a charging island). Nanoparticles forming the capture unit of the present invention are of an opposite charge to SAM structure and are able to contact SAM structure. This contact is typically through an electrostatic interaction. Nanoparticles may be semiconductor nanoparticles, metal nanoparticles, or magnetic colloidal particles. Metal nanoparticles are typically selected from the group consisting of noble metals, alkali metals, alkaline earth metals, Group III metals, transition metals, and Group IV metals. The nanoparticles are prepared by techniques known to one of ordinary skill in the art. In one embodiment, a colloidal solution of oppositely charged nanoparticles is allowed to contact the structure after immersion of the structure into the colloidal solution. The contact and number of contacting nanoparticles is controlled by varying the concentration of the colloidal solution and/or varying the immersion time.

In certain embodiments, the devices of the invention may be based on single electron structures and devices, known in the art. See, for example:

1. V. Ray, R. Subramanian, P. Bhadrachalam, L.-C. Ma, C.-U. Kim, and S. J. Koh, "CMOS-compatible fabrication of room-temperature single-electron devices", *Nature Nanotechnology*, Vol. 3, p. 603-608, 2008;
2. H.-W. Huang, P. Bhadrachalam, V. Ray, and S. J. Koh, "Single-particle placement via self-limiting electrostatic gating", *Applied Physics Letters*, Vol. 93, p. 073110, 2008;
3. L.-C. Ma, R. Subramanian, H.-W. Huang, V. Ray, C.-U. Kim, and S. J. Koh, "Electrostatic Funneling for Precise Nanoparticle Placement: A Route to Wafer-Scale Integration", *Nano Letters*, Vol. 7, p. 439-445, 2007 (Highlighted by MRS in eMatters; January 2007);
4. S. J. Koh, "Strategies for Controlled Placement of Nanoscale Building Blocks", *Nanoscale Research Letters*, Vol. 2, p. 519-545, 2007;
5. S. J. Koh, "Controlled Placement of Nanoscale Building Blocks: Toward Large-Scale Fabrication of Nanoscale Devices", *JOM*, Vol. 59, p. 22-28, 2007; and
6. U.S. Pat. No. 7,465,953;

which are incorporated herein by reference in their entirety.

To form the SAM structure on the dielectric layer, the SAM structure is composed of one or more organic molecules containing functionalized groups (e.g., amino group) at one end capable of holding an electric charge. The other molecular end of SAM structure attaches to the surface atoms of the dielectric layer. A colloidal solution comprising charged nanoparticles is prepared by known methods (e.g., Foss, C A and Feldheim D L, 2001, "Metal Nanoparticles: Synthesis, Characterization, and Application," Dekker, NY, N.Y.) and the structure is dipped into the colloidal solution. Charged nanoparticles then selectively adhere to the exposed sidewall of the dielectric layer that had been functionalized with the charged SAM structure. The charging island is precisely positioned such that the distance between the charging island and the source and drain electrodes is controlled on a nanometer or sub-nanometer scale; and (c) once the single electron structure of the present invention is fabricated, interconnections among individual single electron structures may be processed to produce an integrated circuit. Processing is designed to take advantage of current technologies, including CMOS fabrication technology.

For the fabrication of an integrated circuit comprising structure (or any other single electron device described herein), process steps include those described above after which typical CMOS fabrication steps may be relied upon. Formation of the dielectric layers, formation of one or more self-assembled monolayers, and the contacting of nanoparticles to the self-assembled monolayer(s) of the present invention are compatible with current CMOS fabrication processes. In fact, fabrication of the present invention can be readily and easily integrated into current CMOS manufacturing flow.

With the present invention, there is a well-defined gap between the source electrode and drain electrode. In addition, nanoparticles (e.g., those making up the capture unit) that lie between source and drain are precisely positioned.

Devices of the Invention

The devices of the invention utilize the basic architecture of the single electron structures known in the prior art (such as V. Ray, R. Subramanian, P. Bhadrachalam, L.-C. Ma, C.-U. Kim, and S. J. Koh, "CMOS-compatible fabrication of room-temperature single-electron devices", *Nature Nanotechnology*, Vol. 3, p. 603-608, 2008; and U.S. Pat. No. 7,465,953) with certain specific and important modifications that enable the devices to function is a unique manner. These modifications relative to the prior art structures include:

1. utilizing nanoparticles having single-stranded oligonucleotides attached thereto to form the capture units;
2. positioning the capture units substantially centered on the dielectric layer between the source electrode and the drain electrode; and
3. differentially treated surfaces, i.e., passivating surfaces using self-assembled monolayers to ensure that target molecules only interact with the capture units and not with the remaining surfaces in the device (enabling detection of extremely low quantities of target molecules, even as low as the molecular level).

Accordingly, in one embodiment, the invention is directed to devices, comprising:
an electrically-insulating substrate; and
a first detecting unit, comprising:
  a source electrode disposed on said electrically-insulating substrate;
  a drain electrode; and
  a dielectric layer having a substantially uniform thickness and at least one exposed side;
  wherein said dielectric layer is disposed between said source electrode and said drain electrode;
  wherein said dielectric layer is contiguous with said drain electrode;
  wherein said source electrode, said drain electrode and said dielectric layer are self aligned on said at least one exposed side of said dielectric layer;
  a first self-assembling monolayer attached to and in contact with said at least one exposed side of said dielectric layer (which prior to use may be optionally passivated);
  a second self-assembling monolayer attached to and in contact with said source electrode and said drain electrode;
  wherein said second self-assembling monolayer has a polarity different than the polarity of said first self-assembling monolayer; and
  at least one capture unit, comprising:
    a nanoparticle; and
    a plurality of first single-stranded oligonucleotides attached to said nanoparticle;
    wherein said first single-stranded oligonucleotides have a first nucleotide sequence complementary to a portion of a first oligonucleotide target; and
    wherein said capture unit is located on said exposed side of said dielectric layer and is substantially centered between said source electrode and said drain electrode.

It should be noted that while the capture unit contains single-stranded oligonucleotide, it may also contain a portion of olignonucleotide that is double-stranded. Such capture units are within the scope of the invention, provided that at least a portion of the oligonucleotide in the capture is single-stranded so that it can function to hybridize with the target oligonucleotide.

In another embodiment, the invention is directed to devices described herein, further comprising:
a plurality of second detecting units, each second detecting unit comprising:
  a source electrode disposed on said electrically-insulating substrate;
  a drain electrode; and
  a dielectric layer having a substantially uniform thickness and at least one exposed side;
  wherein said dielectric layer is disposed between said source electrode and said drain electrode;
  wherein said dielectric layer is contiguous with said drain electrode;
  wherein said source electrode, said drain electrode and said dielectric layer are self aligned on said at least one exposed side of said dielectric layer;
  a first self-assembling monolayer attached to and in contact with said at least one exposed side of said dielectric layer (which may be optionally passivated prior to use);
  a second self-assembling monolayer attached to and in contact with said source electrode and said drain electrode;

wherein said second self-assembling monolayer has a polarity different than the polarity of said first self-assembling monolayer; and at least one capture unit, comprising:
a nanoparticle; and
a plurality of at least one second single-stranded oligonucleotides attached to said nanoparticle;
wherein said at least one second single-stranded oligonucleotides have a second nucleotide sequence complementary to a portion of a second oligonucleotide target;
wherein said capture unit is located on said exposed side of said dielectric layer and is substantially centered between said source electrode and said drain electrode;
wherein said second nucleotide sequences are the same or different from said first nucleotides sequences in said first detecting unit; and
wherein said second nucleotide sequences are the same or different from other second nucleotide sequences in said plurality of second detecting units.

In certain embodiments of the invention, the first self-assembling monolayer is positively-charged. In certain embodiments of the invention, the second self-assembling monolayer is negatively-charged or neutral. In certain other embodiments, polarity may be reversed, where the first self-assembled monolayer is negatively charged, but second monolayer is positively charged or neutral.

In certain embodiments of the invention, the nanoparticle is a metal, semiconductor, or magnetic colloidal particle.

In certain embodiments of the invention, the electrically-insulating substrate is silicon, silicon dioxide, or a combination thereof.

In certain embodiments of the invention, the electrically-insulating substrate comprises more than one layer.

In certain embodiments of the invention, wherein said source and drain electrodes comprise a metal selected from the group consisting of gold, silver, titanium, copper, or a combination thereof.

Figure 1:
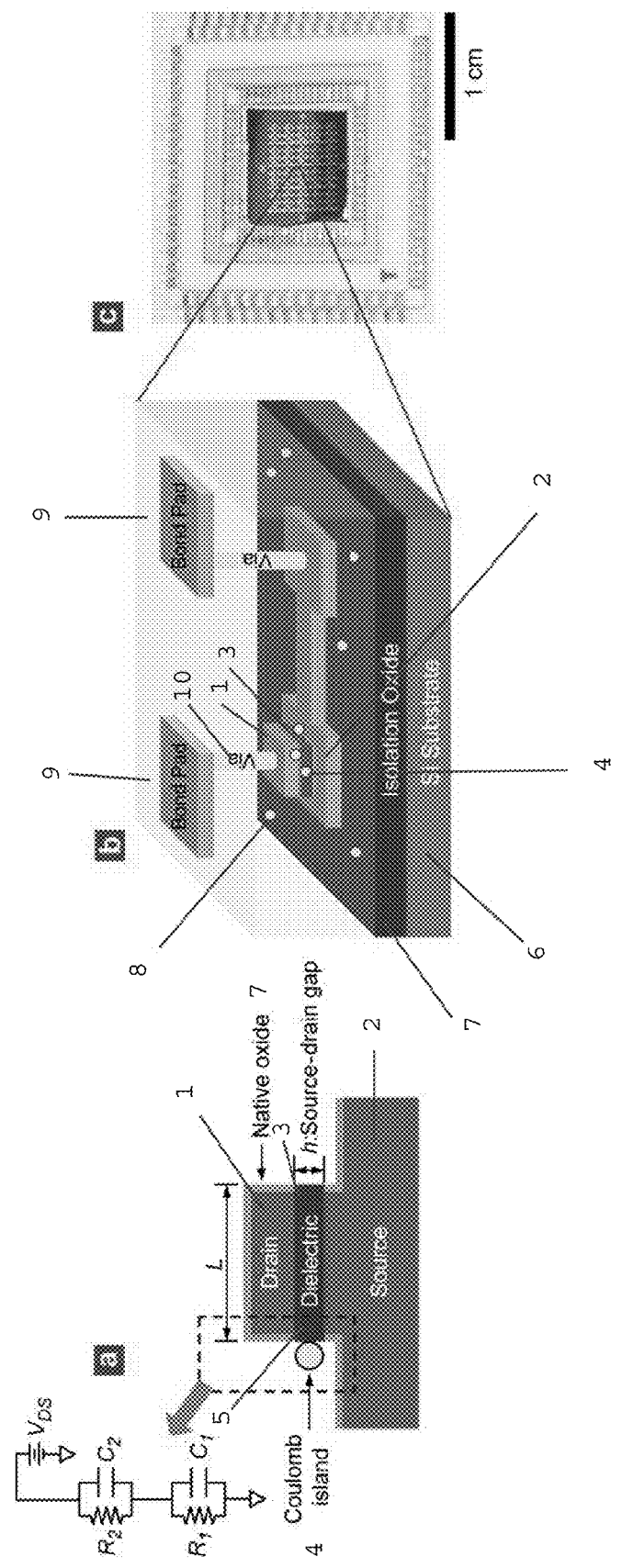
FIG. 1 is a schematic diagram of chip-level fabrication of room-temperature single-electron devices:
(a) Schematic of new single-electron device architecture.
(b) Schematic of one device unit in 3-D.
(c) A photograph of a completed single-electron device chip.

A single-electron device architecture is used in various embodiments of the invention that enables large-scale fabrication of single-electron devices, such as shown in FIG. 1a. There are three key aspects to this new structure. First, the source 2 and drain 1 electrodes are substantially vertically separated by a dielectric layer 3, which enables the control of the source-drain gap h with nanoscale precision over a large area. It should be noted that, while the structure is described as vertically separated, the actual direction of electrodes and dielectric layer is not constrained and may be horizontal or any point there between. Second, the drain/dielectric/source stacks are self-aligned, maintaining the integrity of the source-drain gap h along the periphery of each stack. Third, the Coulomb island 4, that is the capture unit with reference to the invention (shown here without the attached single-stranded nucleic acid sequences visible), is attached on the sidewall 5 of the exposed dielectric film and the single-electron tunneling occurs only at the periphery of the stack, the dotted box in FIG. 1a, so that the lateral dimension, L, can be chosen arbitrarily. This freedom of choosing the lateral dimension makes pattern definition using photolithography possible, enabling single-electron device fabrication in complete parallel processing. With this architecture, room temperature, single-electron devices may be fabricated using CMOS-compatible processes and materials. FIG. 1c shows a photograph of a fabricated chip, with a schematic of one device unit shown in FIG. 1b. FIG. 1b also shows the silicon substrate 6, optional isolation oxide 7, nanoparticles 8 not located on the exposed dielectric layer, bond pads 9 to permit probing by an electric device (not shown), and vias 10.

Figure 2:
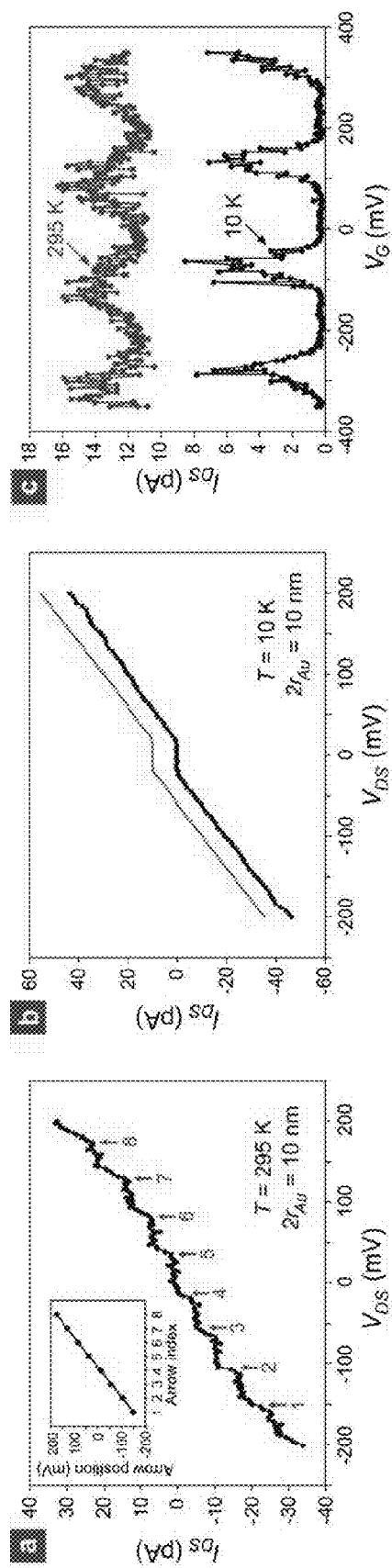
FIG. 2 demonstrates the functioning of the fabricated single-electron devices:
(a) Coulomb staircase at room temperature. Coulomb island: ~10 nm Au nanoparticle (AuNP).
(b) Coulomb blockade at 10K. Coulomb island: ~10 nm AuNP. Blue dots: measured I-V; red line: calculated I-V.
(c) Coulomb oscillation at room temperature (red) and 10K (blue).

The functionality of the fabricated devices has been demonstrated with I-V measurements. FIG. 2a demonstrates the Coulomb staircase, where each step corresponds to an addition/subtraction of a single electron to/from the Coulomb island. FIG. 2b shows the Coulomb blockade (flat region around $V_{DS}=0V$). Single-electron transistors can be fabricated by adding individually addressable gate electrodes. FIG. 2C displays the Coulomb oscillations, i.e., the periodic modulations of the current as a function of the gate voltage, at room temperature and 10 K.

Controlled Placement of Nanoparticles: Electrostatic Funneling

Figure 3:
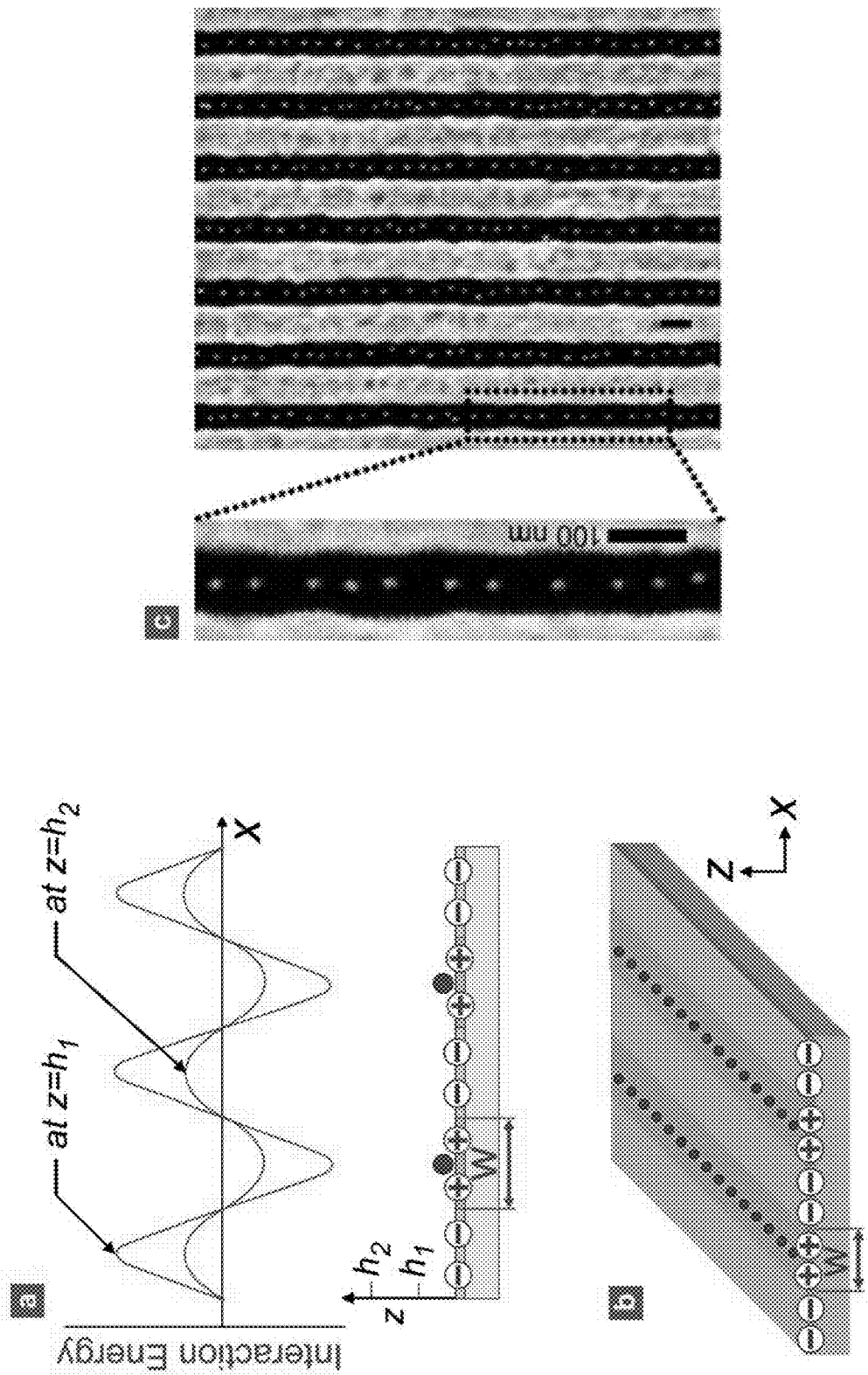
FIG. 3 shows the electrostatic funneling for precise nanoparticle placement on a large scale.

The capability of accurately placing individual nanoscale building blocks (such as nanoparticles, nanowires, proteins, etc.) onto desired substrate locations is one of the key requirements for the fabrication of future nanoscale devices and sensors (including the single-electron devices). A method for placing nanoscale building blocks on a large scale with nanoscale precision is known and it is effective for placing nanoparticles. In this approach, named "electrostatic funneling," charged nanoparticles in a colloid are guided by an electrostatic energy gradient and placed on targeted locations with nanoscale precision. FIGS. 3a and 3b show the concept of electrostatic funneling with a one-dimensional guiding structure as an example. FIG. 3c is an SEM image demonstrating the effectiveness of the electrostatic funneling method. Placement precision of ~6 nm was demonstrated using ~20 nm Au nanoparticles (AuNPs). It is important to note that this nanoscale placement can be carried out on a large scale over an entire substrate since the guiding structure can be defined using common photolithography and accompanying CMOS-compatible processes (note that the line width in FIG. 3 is ~100 nm).

Single-Particle Placement

The ultimate control in the placement of nanoparticles would be the capability of manipulating and positioning them at the single-nanoparticle level, i.e., assigning just one nanoparticle to a specific substrate position. a technique, named "single-particle placement" (SPP), in which exactly one nanoparticle is electrostatically guided and placed onto each target location in a self-limiting way. FIGS. 4(a)-(b) illustrate the SPP concept. First, the substrate surface is functionalized with positively and negatively charged self-assembled monolayers (SAMs), producing an electrostatic guiding structure. When immersed in a nanoparticle colloid, a single nanoparticle is guided and placed at a target position, the circle center in FIG. 4(a). Once a nanoparticle occupies the circle, it alters the electrostatic potential landscape in such a way that the approach of other nanoparticles to the substrate surface is prohibited, resulting in self-limiting SPP, as shown in FIG. 4(b). SEM image in FIG. 5 demonstrates the effectiveness of the SPP.

Single particle placement is further described in the following:

1. V. Ray, R. Subramanian, P. Bhadrachalam, L.-C. Ma, C.-U. Kim, and S. J. Koh, "CMOS-compatible fabrication of room-temperature single-electron devices", *Nature Nanotechnology*, Vol. 3, p. 603-608, 2008;
2. H.-W. Huang, P. Bhadrachalam, V. Ray, and S. J. Koh, "Single-particle placement via self-limiting electrostatic gating", *Applied Physics Letters*, Vol. 93, p. 073110, 2008;
3. L.-C. Ma, R. Subramanian, H.-W. Huang, V. Ray, C.-U. Kim, and S. J. Koh, "Electrostatic Funneling for Precise Nanoparticle Placement: A Route to Wafer-Scale Integration", *Nano Letters*, Vol. 7, p. 439-445, 2007 (Highlighted by MRS in eMatters; January 2007);
4. S. J. Koh, "Strategies for Controlled Placement of Nanoscale Building Blocks", *Nanoscale Research Letters*, Vol. 2, p. 519-545, 2007;
5. S. J. Koh, "Controlled Placement of Nanoscale Building Blocks: Toward Large-Scale Fabrication of Nanoscale Devices", *JOM*, Vol. 59, p. 22-28, 2007; and
6. U.S. Pat. No. 7,465,953;
which are incorporated herein by reference in their entirety.

FIG. 9 illustrates the main concept of the biosensor device of the invention. A structure is provided where source 2 and drain 1 electrodes are vertically separated by a dielectric layer 3, as shown in FIG. 9(a). Nanoparticles (named capture nanoparticles; C-NPs) are selectively placed on the exposed sidewall of the dielectric layer, as shown in FIG. 9(b). The sensor is then brought into a contact with a test solution. If complementary t-ssDNA molecules exist in a test solution, the hybridizations of t-ssDNA with c-ssDNA, and also with p-ssDNA/NP lead to the formation of nanoparticle satellites 11 (NP-SATs where the ssDNA is not visible) around C-NPs 4, as shown in FIG. 9(c). The formation of NP-SATs through DNA hybridizations is schematically shown in FIG. 9(E). Now, when a voltage is applied between the electrodes, the NP-SATs/C-NP conjugates act as current bridges that provide electrical current paths (through direct contact or electron tunneling) across the electrodes, producing current signal, as shown in FIG. 9(d).

For the starting structure in FIG. 9(a), it is noted that that source 2 and drain 1 electrodes are separated vertically and self-aligned. This configuration allows an accurate definition of the source/drain electrode gap h with nanoscale precision by controlling the thickness of the dielectric layer using plasma-enhanced chemical vapor deposition (PECVD). Second, C-NPs 4 (where ssDNA attached to capture unit not shown) are placed at the center locations of the source/drain gap, along the exposed sidewall 5 of the dielectric layer, as shown in FIG. 9(b). This precise placement of C-NPs and also the accurate definition of the electrode gap provide the fundamental geometrical framework of biosensor of the invention.

Third, FIG. 9(c)-(d) indicate that a formation of even a single NP-SATs/C-NP conjugate can, in principle, be electrically detected, making ultra-sensitive t-ssDNA detection on a molecular level possible. In practice, the number of C-NPs attached on the dielectric sidewall may be adjusted and therefore the number of NP-SATs/C-NP conjugates formed across the electrodes (say, a few tens), which increases the detection reliability.

Fourth, the DNA hybridizations are made to occur exclusively on the surface of C-NPs, as shown in FIG. 9(c) and FIG. 9(e). This exclusive hybridization occurs because, in the first place, the c-ssDNA molecules are placed only on the surface of C-NPs. In addition, all the exposed surfaces other than the surfaces of C-NPs are passivated by selectively functionalizing them with self-assembled monolayers (SAMs; not shown in the schematic). The passivated surface prohibits the adsorption of DNA molecules, and any DNA molecule impinging on the passivated surface are returned back to the solution without any loss. Overall, only a small number of t-ssDNA molecules need to be involved in the formation of nanoparticle satellites (NP-SATs/C-NP conjugates), enabling extremely high sensitivity in the t-ssDNA detection.

The molecular-level sensitivity, no requirement of any amplification, and the capability of producing direct electrical output are the key technical merits of the invention.

In certain embodiments, the device further comprises:

a plurality of microfluidic channels; and
an optional cover.

In certain embodiments, the invention is directed to processes for preparing a nano-scale bridging biosensor, comprising:
   forming a device, comprising:
      an electrically-insulating substrate; and
      a first detecting unit, comprising:
         a source electrode disposed on said electrically-insulating substrate;
         a drain electrode; and
         a dielectric layer having a substantially uniform thickness and at least one exposed side;
         a first self-assembling monolayer attached to and in contact with said at least one exposed side of said dielectric layer;
         a second self-assembling monolayer attached to and in contact with said source electrode and said drain electrode;
         wherein said second self-assembling monolayer has a polarity different than the polarity of said first self-assembling monolayer;
         wherein said dielectric layer is disposed between said source electrode and said drain electrode;
         wherein said dielectric layer is contiguous with said drain electrode; and
         wherein said source electrode, said drain electrode and said dielectric layer are self aligned on said at least one exposed side of said dielectric layer;
   providing on said exposed side of said dielectric layer and substantially centered between said source electrode and said drain electrode at least one capture unit, said capture unit comprising:
      a nanoparticle; and
      a plurality of first single-stranded oligonucleotides attached to said nanoparticle; and
      wherein said first single-stranded oligonucleotides have a first nucleotide sequence complementary to a portion of a first oligonucleotide target; and
   passivating said first self-assembling monolayer.

In certain embodiments, the first single-stranded oligonucleotides are attached to said nanoparticle prior to attachment of said capture unit to said exposed side of said dielectric layer.

In certain embodiments, the first single-stranded oligonucleotides are attached to said nanoparticle subsequent to attachment of said capture unit to said exposed side of said dielectric layer.

The device may be fabricated using standard and advanced silicon fabrication techniques.

Standard complementary metal-oxide-semiconductor (CMOS) processes may be used to create an array of detecting units on a single wafer for multiple nucleic acid detection with printed circuit board (PCB) data acquisition and analysis capability.

The design of the chip gives an array of detecting units in which hundreds (n2) of interaction sites may be addressed using a few (2n) probing pads. The probing pads in turn are addressed and controlled using sensitive electronics and software in the manner that pixels in a thin film transistor (TFT) television. This provides an integrated system with on-chip circuitry for data gathering, storage, and analysis. Suitable techniques for addressing the interaction sites at the electrodes in the array are described in the following references, which are incorporated herein by reference in their entirety:
1. A. Hassibi and T. H. Lee, *IEEE Sensors Journal*, 6(6), 1380-1388, (2006);

2. W. F. Aerts, S. Verlaak, and P. Heremans, IEEE Transactions on Electron Devices, 49(12), 2124-2130, (2002); and
3. A. Hassibi, "Integrated Microarrays" Section in *Electrical Engineering*. 2005, Stanford University: Palo Alto, Calif. p. 141.

In alternate embodiments, the invention is directed to devices, comprising:
an electrically-insulating substrate; and
a first detecting unit, comprising:
a source electrode disposed on said electrically-insulating substrate;
a drain electrode; and
a dielectric layer having a substantially uniform thickness and at least one exposed side;
wherein said dielectric layer is disposed between said source electrode and said drain electrode;
wherein said source electrode, said drain electrode and said dielectric layer are in the same plane;
a first self-assembling monolayer attached to and in contact with said dielectric layer (which prior to use may be optionally passivated);
a second self-assembling monolayer attached to and in contact with said source electrode and said drain electrode;
wherein said second self-assembling monolayer has a polarity different than the polarity of said first self-assembling monolayer; and
at least one capture unit, comprising:
a nanoparticle; and
a plurality of first single-stranded oligonucleotides attached to said nanoparticle;
wherein said first single-stranded oligonucleotides have a first nucleotide sequence complementary to a portion of a first oligonucleotide target; and
wherein said capture unit is located on said dielectric layer and is substantially centered between said source electrode and said drain electrode.

Substrate

The devices of the invention include an electrically insulating substrate. The substrate is preferably flat but may take on a variety of alternative surface configurations. The substrate and its surface preferably form a rigid support on which the dielectric layer can be deposited. For instance, the substrate may be any electrically insulating materials. Suitable substrates include, but are not limited to, functionalized glass, Si, Ge, GaAs, GaN, GaP, $SiO_2$, $SiN_4$, modified silicon, semiconductor-on-insulator (SOI), silicon carbide, diamond thin film or any one of a wide variety of gels or polymers such as (poly)tetrafluoroethylene, (poly)vinylidenedifluoride, polystyrene, polycarbonate, polypropylene, or combinations thereof. As is known to those having skill in the art, the substrate may include one or more heteroepitaxial and/or homoepitaxial layers on the substrate. The upper surface of the substrate may be planar or non-planar (three-dimensional). The substrate may be deposited by chemical vapor deposition. Other substrate materials and deposition methods will be readily apparent to those of skill in the art upon review of this disclosure. In a preferred embodiment, the substrate is flat glass or silica with a silicon dioxide layer grown on the surface to provide electrical insulation.

Electrodes

In certain embodiments, the source and drain electrodes comprise a metal selected from the group consisting of gold, silver, titanium, copper, or a combination thereof.

Nanoimprint lithography may be used to fabricate the electrodes. The electrodes may be formed into an array where each nanogap is individually addressed with metal lines (bus-bars), preferably running at right angles. Each mutually-insulated intersection of the addressing lines contacts one electrode pair that serves as the binding and sensing site of the probe-target hybridization. The bus lines may be fabricated in two layers with electrical isolation between the two layers achieved by chemical vapor deposition (CVD) of silicon nitride.

The structure may be covered with microfluidic channels. The electrical isolation may be achieved by sequential and automated measurement of each pair of electrodes.

In certain embodiments, nanopatterns may be made on an oxidized silicon wafer using e-beam lithography (EBL). The EBL patterns may be used to fabricate the stamp for the nanoelectrode fabrication. The EBL patterns may be used to remove silicon dioxide and then silicon from the non-patterned areas using deep reactive ion etching (DRIE). Silicon dioxide acts as a hard mask during the process, resulting is a high aspect ratio nano-scale linear island features in silicon having the same dimensions as required the nanogap electrodes. The wafer may act as a stamping mask for NIL. In NIL, a polymer layer is spun on the wafer and a stamping wafer is compressed on the polymer to transfer the pattern. One stamp can be used multiple times and one stamping takes a few minutes to transfer the nano-scale patterns in the polymer. Standard lift-off process may be carried out to create the metal lines at the nanoscale from these stamp-defined patterns. In certain embodiments of the lift-off process, metal stays only in the NIL transferred nanoelectrode structure and the remainder of the metal lifts off in an ultra-sonicator assisted solvent soak. The first layer of addressing electrodes/bus may then be using standard optical lithography aligned to the nano-scale metal lines. The second layer of metal lines/bus may be deposited after CVD deposition of silicon nitride and reactive ion etch opening of small micron sized windows in the silicon nitride above the nanogap electrodes.

Self-Assembled Monolayers

The formation of self-assembled monolayers is used to precisely place the capture units. More specifically, first and second self-assembled monolayers, which form an electrostatic funneling (guiding) structure, enable the placement of capture nanoparticles (capture units) on the center region between the two electrodes.

Passivation: Prior to exposure to target, the first self-assembled monolayer on the dielectric layer is modified (passivated) to produce different polarity. For example, the positively-charged self-assembled monolayers can be changed so that the terminal group of the molecular layers are terminated by non-polar or negatively charged molecules. Examples of this modification (passivation) are displayed in FIGS. 13 and 14. This passivation ensures that the DNA or protein molecules do not attach to the dielectric surface, thereby increasing the probability that the target DNA or protein finds the surface of capture units the only possible place for hybridization or antigen-antibody reaction.

SAM structures generally comprise an organic or inorganic molecule or compound with a tail group that holds electric charge, such as an amino group ($—NH_2$ with a positive charge) or carboxyl group ($—COOH$ with a negative charge). The molecule selected is not dependent upon a specific chemistry but must be one that has affinity for nanoparticle adhesion and must be capable of forming a monolayer-like structure.

In the device of the invention, the first self-assembling monolayer is attached to and in contact with said at least one exposed side of said dielectric layer. The second self-assembling monolayer is attached to and in contact with said source electrode and said drain electrode, wherein said second monolayer has a polarity different than the polarity of said first monolayer. In certain embodiments of the invention, the first self-assembling monolayer is positively-charged. In certain embodiments of the invention, the second self-assembling monolayer is negatively-charged or neutral. Differentially treated surfaces, i.e., using two different surface-assembled monolayers, ensure that target molecules only interact with the capture units and not with the remaining surfaces in the device (enabling detection of extremely low quantities of target molecules, even as low as the molecular level).

In the biosensor of the inventor, the presence of single-stranded oligonucleotide target (t-ssDNA) molecules leads to, through DNA hybridization (as illustrated in FIG. 9(e)), the formation of nanoparticle satellites (NP-SATs) around the C-NPs, FIG. 9(c). The important feature of the approach is that the DNA hybridization is carried out only on C-NPs. For this exclusive hybridization to be successful, it is essential that when migrating DNA molecules impinge on any surface except for that of C-NPs, they should not be adsorbed, but returned back into the solution so that they remain available for hybridization. Since DNA molecules are negatively charged, undesired adsorption can be prevented by passivating the silicon oxide surface using negatively-charged or non-polar molecules. There are a number of approaches for passivating the silicon oxide surface and forming NP-SATs around the C-NPs, such as those shown in FIG. 13. The source and drain electrodes (Au) are functionalized with 16-mercaptohexadecanoic acid (MHA; —COO— terminated; negatively charged), which repel DNA molecules.

For the first approach, Scheme 1 (top in FIG. 13), a silicon oxide surface is functionalized with SAMs of 3-aminoprophyl)triethoxysilane (APTES; —$NH_3$ terminated; positively charged). Immersion of the wafer into a colloid containing C-NPs (Au nanoparticles (AuNPs); negatively charged) leads to attachment of C-NPs on the APTES functionalized surface, FIG. 13-S1(a). Then, the terminating amine group (—$NH_3^+$) of APTES SAMs is modified by reacting with acetic acid ($CH_3COOH$), producing a surface terminated by methyl groups ~(—$CH_3$; non-polar), FIG. 13-S1(b). The methyl terminated surface provides the passivation, and when c-ssDNA molecules are introduced they are immobilized on the C-NP surface (Au) due to the chemical bonding between thiol (—SH) group of the c-ssDNA and the Au surface of the C-NP, FIG. 13-S1(c). (The structure of thiol modified c-ssDNA is shown in FIG. 15.) At this point, the device is ready for further DNA hybridization, with the procedure in FIG. 9(e), to produce NP-SATs/C-NP conjugates, FIG. 13 (the rightmost).

Another approach, Scheme 2 (bottom in FIG. 13), may also be used. The main difference from the previous approach is that c-ssDNA molecules are pre-attached to C-NPs prior to placing the C-NPs on the silicon oxide surface. As in the previous, ATPES SAMs are selectively formed on the silicon oxide surface, FIG. 13 (the leftmost). A solution containing c-ssDNA/C-NPs is prepared and brought into a contact with the silicon oxide surface, and the c-ssDNA/C-NPs attach on the APTES surface, FIG. 13-S2(a). Then, the amine group of APTES SAMs will be reacted with PITC (phenyl isothiocyanate; $C_6H_5NCS$), passivating the silicon oxide surface with negatively charged benzene group, FIG. 13-S2(b). (Here, PITC is used because PITC solution does not degrade DNA, whereas acetic acid solution does.)

Capture Units

The capture units (referred to herein c-NP) used in the devices, systems, and methods of the invention comprise:
  a nanoparticle; and
  a plurality of first single-stranded oligonucleotides attached to said nanoparticle;
  wherein said first single-stranded oligonucleotides have a first nucleotide sequence complementary to a portion of a first oligonucleotide target; and
  wherein said capture unit is located on said exposed side of said dielectric layer and is substantially centered between said source electrode and said drain electrode.

Oligonucleotides of defined sequences are used for a variety of purposes in the practice of the invention. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues,* 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

The selection of capture units and their organization in an array depends upon the use to which the biological chip will be put. In one embodiment, the chips are used to sequence or re-sequence nucleic acid molecules, or compare their sequence to a reference molecule. Re-sequencing nucleic acid molecules involves determining whether a particular molecule has any deviations from the sequence of reference molecule.

In typical diagnostic applications, a solution containing one or more targets to be identified (i.e., samples from patients) contacts the probe array. The targets will bind or hybridize with complementary probe sequences. Accordingly, the probes will be selected to have sequences directed to (i.e., having at least some complementarity with) the target sequences to be detected, e.g., human or pathogen sequences. The nanoparticle reporter conjugates only hybridize with those probes where there has been a binding event with a target, permitting an electrical current to be detected at known locations. Accordingly, locations at which targets hybridize with complimentary probes can be identified by locating the electrical current in an electrode set. Based on the locations of the electrodes where hybridization occurs, information regarding the target sequences can be extracted. The existence of a mutation may be determined by comparing the target sequence with the wild type.

Individual probe sequence may be designed to detect known single nucleotide base mutations, such as, for example, the K-ras mutation described in the examples, which is a prognostic indicator for lung cancer, other cancers, cystic fibrosis, and sickle cell anemia. However, the invention is not limited to methods of detecting known single nucleotide base mutations, but may be used to identify the nucleic acid sequence of any desired target.

The nanoparticles, the oligonucleotides, or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry,* Houston, Tex., pages 109-121 (1995). See also, Mucic et al., *Chem. Commun.* 555-557 (1996), which describes a method of attaching 3' thiol DNA to flat gold surfaces; this method can be used to attach oligonucleotides to nanoparticles. The alkanethiol method can also be used to attach oligonucleotides to other metal, semiconductor, and magnetic colloids and to the other nanoparticles listed above.

Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods that may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman, et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec, et al., *J. Phys. Chem.*, 92, 2597 (1988) (rigid phosphates on metals).

Oligonucleotides functionalized with a cyclic disulfide are within the scope of this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Preferably, the optional linker further comprises a hydrocarbon moiety attached to the cyclic disulfide. Suitable hydrocarbons are available commercially, and are attached to the cyclic disulfides. Preferably the hydrocarbon moiety is a steroid residue. Oligonucleotide-nanoparticle conjugates prepared using linkers comprising a steroid residue attached to a cyclic disulfide are stable to thiols (e.g., dithiothreitol used in polymerase chain reaction (PCR) solutions) as compared to conjugates prepared using alkanethiols or acyclic disulfides as the linker. This stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

The capture units may be directed to and located on the exposed side of the dielectric layer using electrostatic funneling. Different oligonucleotide probes, referred herein as "second oligonucleotide probes," may be localized at their respective electrodes by providing the second oligonucleotide probes and sequentially energizing the desired set(s) of electrodes to direct and localize the second oligonucleotide probes in the appropriate location. This procedure may be repeated until all of the different oligonucleotide probes are directed to and located on the exposed side of the dielectric layer between their desired set(s) of electrodes.

Microfluidic Channels

Assays on biological arrays generally include contacting a probe array with a sample under the selected reaction conditions, optionally washing the well to remove unreacted molecules, and analyzing the biological array for evidence of reaction between target molecules and the probe molecules. These steps involve handling fluids. Microfluidic channels may be used to deliver the liquids to the test sites made from any suitable solid material, such as polydimethylsiloxane. The methods of this invention automate these steps so as to allow multiple assays to be performed concurrently. Accordingly, this invention employs automated fluid handling systems for concurrently performing the assay steps in each of the test wells. Fluid handling allows uniform treatment of samples in the test sites. Microtiter robotic and fluid-handling devices are available commercially, for example, from Tecan AG.

The device may be introduced into a holder in the fluid-handling device. This robotic device may be programmed to set appropriate reaction conditions, such as temperature, add samples to the device, incubate the test samples for an appropriate time, remove unreacted samples, wash the wells, add substrates as appropriate and perform detection assays. The particulars of the reaction conditions depend upon the purpose of the assay. For example, in a sequencing assay involving DNA hybridization, standard hybridization conditions are chosen. However, the assay may involve testing whether a sample contains target molecules that react to a probe under a specified set of reaction conditions. In this case, the reaction conditions are chosen accordingly.

DNA Array Chips/Multiplex DNA Sensing

As shown in FIGS. 9 and 10, the fabrication of the device of the invention may be carried out within the framework of current CMOS fabrication technology. This means that arrays of sensor units can be built on a large scale over an entire wafer in parallel processing. When this capability is combined with well-established DNA microarray technology (which currently can assay hundreds of thousands of different DNA sequences simultaneously), DNA detection technology leads to multiplex DNA sensing, but with sensitivity of detecting extremely low concentrations of unknown t-ssDNA molecules. Importantly, the output is an electrical signal, which will have tremendous advantages in data handling over the typical optical (fluorescent) output of current DNA microarray technology.

Systems

In other aspects, the invention is directed to systems, comprising:
  a device described herein; and
  a plurality of nanoparticle reporter conjugates (referred to herein as the NP-SATs);
    wherein said nanoparticle reporter conjugates comprise at least one nanoparticle and a single-stranded oligonucleotide complementary to at least a portion of said first oligonucleotide target different than said portion complementary to said first nucleotide sequence; and
    wherein said nanoparticle is a metal, semiconductor, or magnetic colloidal particle.

In other aspects, the invention is directed to systems, comprising:
- a multiplexing device described herein;
- a plurality of first nanoparticle reporter conjugates; and
- a plurality of at least one second nanoparticle reporter conjugates;
- wherein said first nanoparticle reporter conjugates comprise at least one nanoparticle and a single-stranded oligonucleotide complementary to at least a portion of said first oligonucleotide target different than said portion complementary to said first nucleotide sequence;
- wherein said nanoparticle in said first nanoparticle reporter conjugate is a metal, semiconductor, or magnetic colloidal particle;
- wherein said at least one second nanoparticle reporter conjugates comprise at least one nanoparticle and a single-stranded oligonucleotide complementary to at least a portion of said at least one second oligonucleotide target different than said portion complementary to said at least one second nucleotide sequence;
- wherein said nanoparticle in said at least one second nanoparticle reporter conjugate is a metal, semiconductor, or magnetic colloidal particle;
- wherein said second nanoparticle reporter conjugates are the same or different from said first nanoparticle reporter conjugates; and
- wherein said second nanoparticle reporter conjugates are the same or different from said other second nanoparticle reporter conjugates.

In further embodiments, the systems further comprise:
an electrical reading device for interrogating said device described herein.

In certain preferred embodiments, said electrical reading device is portable.

Nanoparticle Reporter Conjugates

The nanoparticle reporter conjugates of the invention comprise at least one nanoparticle (either a metal, semiconductor, or magnetic colloidal particle) and a single-stranded oligonucleotide complementary to at least a portion of said first oligonucleotide target different than said portion complementary to said first nucleotide sequence. In certain embodiments, the nanoparticle reporter conjugates further comprise a linker. While not wishing to be bound by theory, it is believed that the nanoparticle reporter conjugates hybridize with at least a portion of said first oligonucleotide target different than said portion complementary to said first nucleotide sequence. This hybridization facilitates the movement of electrons, at least partially due to the π-stacking of base pairs of the nucleic acids in the double helix structure, thereby increasing the charge conduction between the source and drain electrodes. The hybridization of the single-stranded oligonucleotide probe in the capture unit with perfectly complementary targets, and their subsequent hybridization with the nanoparticle reporter conjugates permits charge transport, thus making electrical detection possible. In addition, there is direct contact between the electrodes due to the hybridization of the nanoparticle reporter conjugates forming the nanoparticle satellites.

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials. In certain embodiments, metal nanoparticles, especially gold nanoparticles, are preferred. The use of semiconductor and magnetic particles permits the use of the same system for multi-modal detection, including capacitance change, impedance change, or from field effect, for example. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The nanoparticles may also be rods.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988), all of which are incorporated herein by reference.

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshaysky et al., *J. Am. Chem. Soc.*, 112, 9438 (1990); Ushida et al., *J. Phys. Chem.*, 95, 5382 (1992), all of which are incorporated herein by reference.

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles because of their stability, ease of imaging by electron microscopy, and well-characterized modification with thiol functionalities.

The nanoparticles, the oligonucleotides, or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry*, Houston, Tex., pages 109-121 (1995). See also, Mucic et al., *Chem. Commun.* 555-557 (1996), which describes a method of attaching 3' thiol DNA to flat gold surfaces; this method can be used to attach oligonucleotides to nanoparticles. The alkanethiol method can also be used to attach oligonucleotides to other metal, semiconductor, and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoakylsiloxanes). Oligonucleotides terminated with a 5' thionucleoside or a 3' thionucleoside may also be used for attaching oligonucleotides to solid surfaces. The following references describe other methods that may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid*

*Interface Sci.,* 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.,* 69, 984-990 (1965) (carboxylic acids on platinum); Soriaga and Hubbard, *J. Am. Chem. Soc.,* 104, 3937 (1982) (aromatic ring compounds on platinum); Hubbard, *Acc. Chem. Res.,* 13, 177 (1980) (sulfolanes, sulfoxides and other functionalized solvents on platinum); Hickman et al., *J. Am. Chem. Soc.,* 111, 7271 (1989) (isonitriles on platinum); Maoz and Sagiv, *Langmuir,* 3, 1045 (1987) (silanes on silica); Maoz and Sagiv, *Langmuir,* 3, 1034 (1987) (silanes on silica); Wasserman, et al., *Langmuir,* 5, 1074 (1989) (silanes on silica); Eltekova and Eltekov, *Langmuir,* 3, 951 (1987) (aromatic carboxylic acids, aldehydes, alcohols and methoxy groups on titanium dioxide and silica); Lec, et al., *J. Phys. Chem.,* 92, 2597 (1988) (rigid phosphates on metals).

Oligonucleotides functionalized with a cyclic disulfide are within the scope of this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Preferably, the optional linker further comprises a hydrocarbon moiety attached to the cyclic disulfide. Suitable hydrocarbons are available commercially, and are attached to the cyclic disulfides. Preferably the hydrocarbon moiety is a steroid residue. Oligonucleotide-nanoparticle conjugates prepared using linkers comprising a steroid residue attached to a cyclic disulfide are stable to thiols (e.g., dithiothreitol used in polymerase chain reaction (PCR) solutions) as compared to conjugates prepared using alkanethiols or acyclic disulfides as the linker. This stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

Further description of the formation of nanoparticle conjugate structures (including nanoparticle satellites) may be found in:
1. X. Y. Xu, N. L. Rosi, Y. H. Wang, F. W. Huo, C. A. Mirkin. Asymmetric functionalization of gold nanoparticles with oligonucleotides. Journal of American Chemical Society, 128, 9286 (2006); and
2. F. W. Huo, A. K. R. Lytton-Jean, C. A. Mirkin. Asymmetric functionalization of nanoparticles based on thermally addressable DNA interconnects. Advanced Materials, 18, 2304 (2006);
which are incorporated herein by reference in their entirety.
Electrical Reader Suitable electrical reading devices include any device for low power printed circuit board electronics capable of measuring either sequentially or in parallel a small change in conductivity, resistivity, capacitance, or impedance in a pico-ampere range. The Agilent 4155C semiconductor parameter analyzer and the Agilent 4156C semiconductor parameter analyzer are examples of suitable devices.
Methods of Use The invention provides a nanotechnology-based low-power, rapid, inexpensive, recyclable, and sensitive electrical detection device, system, and method of molecular level concentrations of nucleic acid sequences, including genes, and amino acid sequences with no external sample preparation or labeling or other chemical modification of the sample. The biosensors of the invention may be used in wide variety of applications requiring sensitive nucleic acid sequence and amino acid sequence detection, including, but not limited to, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

In one aspect, the invention is directed to methods for detecting nucleic acid hybridization, comprising:
  providing a device described herein;
  passivating said first self-assembling monolayer;
  providing a solution comprising at least one buffer and single-stranded oligonucleotide target under hybridizing conditions;
    wherein said single-stranded oligonucleotide target hybridizes a portion of said first nucleotide sequence thereby leaving an unhybridized portion of said single-stranded oligonucleotide target;
  providing a plurality of first nanoparticle reporter conjugates under hybridizing conditions;
    wherein said first nanoparticle reporter conjugates comprise at least one nanoparticle and an oligonucleotide complementary to said unhybridized portion of said single-stranded oligonucleotide target;
    wherein said nanoparticle in said first nanoparticle reporter conjugate is a metal, semiconductor, or magnetic colloidal particle;
  applying a voltage drop across said electrodes; and
  measuring a change in conductivity, resistivity, capacitance, or impedance across said electrodes at known locations to determine perfect complementarity of said oligonucleotide target to said first oligonucleotide sequence.

In certain embodiments, the measuring step measures an increase in conductivity across said electrodes at known locations to determine perfect complementarity of said oligonucleotide target to said first oligonucleotide sequence.

In certain embodiments, the single-stranded oligonucleotide target is prepared by heating a solution comprising double-stranded oligonucleotide target.

In certain embodiments, the methods further comprises:
  washing to remove unhybridized components from said detecting unit.

In certain embodiments, the methods further comprises:
  heating a solution comprising double stranded oligonucleotide target to form said solution comprising single-stranded oligonucleotide target.

In certain embodiments, the methods comprise:
  providing a multiplexing device described herein;
  passivating said first self-assembling monolayer;
  providing a solution comprising at least one buffer and single-stranded oligonucleotide target under hybridizing conditions;

wherein said single-stranded oligonucleotide target hybridizes a portion of said at least one second nucleotide sequence thereby leaving an unhybridized portion of said single-stranded oligonucleotide target;

providing a plurality of at least one second nanoparticle reporter conjugates under hybridizing conditions;

wherein said second nanoparticle reporter conjugates comprise at least one nanoparticle and an oligonucleotide complementary to said unhybridized portion of said single-stranded oligonucleotide target;

wherein said nanoparticle in said second nanoparticle reporter conjugate is a metal, semiconductor, or magnetic colloidal particle;

wherein said second nanoparticle reporter conjugates are the same or different from said first nanoparticle reporter conjugates;

wherein said second nanoparticle reporter conjugates are the same or different from said other second nanoparticle reporter conjugates;

wherein said measuring step is carried out in parallel or sequentially for said first detecting unit and said plurality of said additional detecting units.

It would be desirable to detect the single-stranded oligonucleotide target in as short time as possible, which requires enhancing the hybridization kinetics. Over the past decade, there have been intensive studies toward efficient DNA hybridization. Using microfluidic microarrays and re-circulation mixing (called shuttle hybridization), Cheng and co-workers demonstrated hybridization time as short as ~8 minutes for target concentration of 19 aM with 1 μl sample volume (Wei, C. W., Cheng, J. Y., Huang, C. T., Yen, M. H. & Young, T. H. Using a microfluidic device for 1 ml DNA microarray hybridization in 500 s. *Nucleic Acids Research* 33, e78 (2005)). Similarly short hybridization times, ranging from 5 to 60 minutes, have been reported by others as well for target concentrations ranging from 10 pM to 20 fM, also for microfluidic microarray setups. (Benn, J. A., Hu, J., Hogan, B. J., Fry, R. C., Samson, L. D. and Thorsen, T. Comparative modeling and analysis of microfluidic and conventional DNA microarrays. *Analytical Biochemistry* 348, 284-293 (2006); Lee, H. J., Goodrich, T. T. & Corn, R. M. SPR imaging measurements of 1-D and 2-D DNA microarrays created from microfluidic channels on gold thin films. *Analytical Chemistry* 73, 5525-5531 (2001)). Considering that the device of the invention needs a much smaller number of t-ssDNA molecules to produce a signal (even one NP-SATs/C-NP conjugate that bridges source and drain electrodes will produce a signal), the hybridization time of the devices of the invention can be made short (<1 hour), if hybridization enhancement techniques including microfluidics/forced convection and control of film thickness of the solution.

In certain embodiments, the methods further comprise:
washing to remove unhybridized components from said detecting unit.

In certain embodiments, the methods further comprise:
heating said device to remove said hybridized targets and said hybridized nanoparticle reporter conjugates from said probe to permit recycling of said detecting unit.

In certain embodiments, the methods further comprise:
heating a solution comprising double stranded oligonucleotide target to form said solution comprising single-stranded oligonucleotide target.

In certain embodiments, the methods further comprise:
forming a temperature gradient to focus said single stranded oligonucleotide target at said detecting unit.

In certain embodiments, the methods further comprise:
applying an electric field to direct said single-stranded oligonucleotide target to said capture unit to reduce the hybridization time.

The methods of the invention may be used to quantify the level of oligonucleotides or polypeptides. For example, the change in conductance (or other electrical characteristic) between nanogaps is direct function of the number of nanoparticles located between nanogaps. The number of nanoparticles is a direct function of the number of perfectly complementary oligonucleotides that have hybridized. Thus, the change of conductivity (or other electrical characteristic) can be directly correlated to the quantity of perfectly complementary oligonucleotides or polypeptides present in the sample.

In certain embodiments, said voltage drop is applied as direct current. In other embodiments, said voltage drop is applied as alternating current and the alternating current impedance measured.

In certain embodiments, said measuring step measures an increase in conductivity across said electrodes at known locations to determine perfect complementarity of said oligonucleotide target to said first oligonucleotide probes.

In certain embodiments, said single-stranded oligonucleotide target is prepared by heating a solution comprising double-stranded oligonucleotide target.

In certain embodiments, the invention is directed to methods for detecting nucleic acid hybridization, comprising the optional step to enhance detection of the nucleic acid of reversibly exchanging an imino proton in each base pair of the reporter conjugate or capture oligonucleotide probes with a metal ion selected from the group consisting of gold ion, silver ion, platinum ion, and copper ion. The reversible exchanging of an imino proton in each base pair may be carried out as described in A. Rakitin, Aich, P., Papadopoulos, C., Kobzar, Yu., Vedeneev, A. S., Lee, J. S., J. M. Xu, *Phys. Rev. Lett.,* 86(16), 3670-3673, (2001), which is incorporated herein by reference.

In certain embodiments, the invention is directed to methods for detecting nucleic acid hybridization, comprising the optional step to enhance detection of the nucleic acid of vectorially depositing silver on said double stranded nucleic acid sequence. In certain embodiments of this method, the vectorially depositing step comprises: ion exchanging silver ions on said double stranded nucleic acid sequence; reducing said silver ions; and developing silver aggregates on said double stranded nucleic acid sequence; as described in E. Braun, Y. Eichen, U. Sivan, and G. Ben-Yoseph, *Nature,* 391(6669), 775-778, (1998), incorporated herein by reference.

In certain embodiments, the invention is directed to methods for detecting nucleic acid hybridization, comprising the optional step to enhance detection of the nucleic acid of providing a solution comprising nanoparticle polypeptide conjugates; wherein the nanoparticle polypeptide conjugates comprise at least one nanoparticle and a polypeptide, preferably comprising at least one residue of cysteine, that binds to said double stranded oligonucleotide-stem complex.

Protein Sensor

The device and systems of the invention may be modified to be used for detecting protein molecules of small molecular weight. The main difference from the nucleic acid sensor is that the nanoparticle satellite formation is done via protein-antibody reaction rather than nucleic acid hybridization. The ability of detecting extremely small concentrations of target protein molecules is particularly important, since, at this moment, there exists no method of amplifying proteins.

Thus, in certain embodiments, the invention is directed to such protein devices, comprising:

an electrically-insulating substrate; and
a first detecting unit, comprising:
- a source electrode disposed on said electrically-insulating substrate;
- a drain electrode; and
- a dielectric layer having a substantially uniform thickness and at least one exposed side;
- wherein said dielectric layer is disposed between said source electrode and said drain electrode;
- wherein said dielectric layer is contiguous with said drain electrode;
- wherein said source electrode, said drain electrode and said dielectric layer are self aligned on said at least one exposed side of said dielectric layer;
- a first self-assembling monolayer attached to and in contact with said at least one exposed side of said dielectric layer (which may be optionally passivated prior to use);
- a second self-assembling monolayer attached to and in contact with said source electrode and said drain electrode;
- wherein said second self-assembling monolayer has a polarity different than the polarity of said first self-assembling monolayer; and
- at least one capture unit, comprising:
  - a nanoparticle; and
  - a plurality of first antibodies attached to said nanoparticle;
  - wherein said first antibody have affinity to a portion of a first polypeptide target; and
  - wherein said capture unit is located on said exposed side of said dielectric layer and is substantially centered between said
- source electrode and said drain electrode.

In other embodiments, the invention is directed to methods of detecting protein-antibody interaction, comprising:
- providing a protein device described above;
- passivating said first self-assembling monolayer;
- providing a solution comprising at least one buffer and polypeptide target under binding conditions;
  - wherein a portion of said polypeptide target binds said first antibody;
- providing a plurality of first nanoparticle reporter conjugates under hybridizing conditions;
  - wherein said first nanoparticle reporter conjugates comprise at least one nanoparticle and a second antibody capable of binding the unbound portion of said polypeptide target;
  - wherein said nanoparticle in said first nanoparticle reporter conjugate is a metal, semiconductor, or magnetic colloidal particle; applying a voltage drop across said electrodes; and
- measuring a change in conductivity, resistivity, capacitance, or impedance across said electrodes at known locations to determine perfect binding of said polypeptide target to said first antibody.

The capture units comprising the antibody and nanoparticle and nanoparticle reporter conjugates comprising the antibody and nanoparticle may be prepared in accordance with techniques known in the art such as those described in 1. J. M. Nam, C. S. Thaxton, C. A. Mirkin. Nanoparticle-based bio-bar codes for the ultrasensitive detection of proteins. *Science* 301, 1884 (2003) and references cited therein; and
2. M. De, P. S. Ghosh, V. M. Rotello. Applications of Nanoparticles in Biology. *Advanced Materials* 20, 4225 (2008) and references cited therein.

The antibody-nanoparticle conjugates are commercially available for example from Ted Pella, Inc.

The methods of this invention will find particular use wherever high through-put of samples is required. In particular, this invention is useful in clinical settings and for sequencing large quantities of DNA, RNA, or protein, especially at low concentrations in the molecular level range.

The clinical setting requires performing the same test on many patient samples. The automated methods of this invention lend themselves to these uses when the test is one appropriately performed on a biological chip. For example, a DNA array can determine the particular strain of a pathogenic organism based on characteristic DNA sequences of the strain. The advanced techniques based on these assays now can be introduced into the clinic. Fluid samples from several patients are introduced into the test wells of a biological chip plate and the assays are performed concurrently.

In some embodiments, it may be desirable to perform multiple tests on multiple patient samples concurrently. According to such embodiments, rows (or columns) of the microtiter plate will contain probe arrays for diagnosis of a particular disease or trait. For example, one row might contain probe arrays designed for a particular cancer, while other rows contain probe arrays for another cancer. Patient samples are then introduced into respective columns (or rows) of the microtiter plate. For example, one column may be used to introduce samples from patient "one," another column for patient "two" etc. Accordingly, multiple diagnostic tests may be performed on multiple patients in parallel. In still further embodiments, multiple patient samples are introduced into a single well. In a particular well indicator the presence of a genetic disease or other characteristic, each patient sample is then individually processed to identify which patient exhibits that disease or trait. For relatively rarely occurring characteristics, further order-of-magnitude efficiency may be obtained according to this embodiment.

Particular assays that will find use in automation include those designed specifically to detect or identify particular variants of a pathogenic organism, such as HIV. Assays to detect or identify a human or animal gene are also contemplated. In one embodiment, the assay is the detection of a human gene variant that indicates existence of or predisposition to a genetic disease, either from acquired or inherited mutations in an individual DNA. These include genetic diseases such as cystic fibrosis, diabetes, and muscular dystrophy, as well as diseases such as cancer (the P53 gene is relevant to some cancers), as disclosed in U.S. Pat. No. 5,837,832.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1

Formation of Self-Aligned Drain/Dielectric/Source Structure (Step a in FIG. 9)

FIG. 10 displays process steps to achieve the vertically self-aligned drain/dielectric/source structure, the starting configuration in FIG. 9(a). First, a stack of films is made on a silicon wafer using standard CMOS fabrication techniques including thermal oxidation (isolation oxide), metal evaporation (source electrode 2; Au/Cr), and PECVD 3 (silicon oxide), as shown in FIG. 10(a). On top of this film stack, the drain electrode 1 (Au) is made using photolithography, evaporation of Au/Cr, and lift-off, as shown in FIG. 10(b). The lateral dimension of the drain electrode is on the order of ~100 μm, so that the drain electrode can be easily contacted by an electrical probe during I-V measurement. Then, using the drain electrode 1 as a hard mask, the wafer is vertically etched using reactive ion etching (RIE), producing self-aligned drain/oxide/source structure, as shown in FIG. 10(a). (The PECVD oxide is etched using $CF_4$ chemistry, with over-etching removing top portion of the source electrode.) It is important to note that due to the substantial self-alignment, the integrity of source/drain separation is maintained without regard to the actual shape or size of the drain electrode.

The fabrication of similar self-aligned drain/dielectric/source structure during the fabrication of single-electron transistors has been demonstrated (See, for example, U.S. Pat. No. 7,465,953; and Ray, V., Subramanian, R., Bhadrachalam, P., Ma, L. C., Kim, C. U. & Koh, S. J. CMOS-compatible fabrication of room-temperature single-electron devices. *Nature Nanotechnol.* 3, 603-608 (2008), incorporated herein by reference in its entirety). Relative to the single-electron transistors, the biosensors of the invention need a much thicker dielectric layer (for example, PECVD oxide of ~100 nm instead of ~10 nm) and preferably also different electrode materials (Au instead of Cr).

Example 2

Precise Placement of the C-NPs (Step b in FIG. 9)

The next requirement is the precise placement of C-NPs along the substantially center positions of the exposed dielectric sidewall, FIG. 9(b). To achieve this, "electrostatic funneling" method is used which, as described earlier (see FIG. 3), is proven effective for placing nanoparticles on a planar surface. To demonstrate the feasibility of accurately placing C-NPs on the sensor structure, FIG. 9(b), similar three-dimensional step structures was fabricated having differing oxide thicknesses and applied the electrostatic funneling method, FIG. 11. As is clear from the scanning electron micrograph (SEM) images, nanoparticles having differing diameters (~200, ~80, and ~50 nm for FIG. 11(a), (b), and (c), respectively) were placed along the center positions of the exposed oxide sidewalls. In this demonstration, the source and drain electrodes were functionalized with negatively charged SAMs (16-mercaptohexadecanoic acid; MHA) while the exposed silicon oxide sidewalls functionalized with positively charged SAMs ((3-aminoprophyl)triethoxysilane; APTES), producing electrostatic guiding structure that forces the Au nanoparticles (NPs) (negatively charged with citrate ions) onto the center locations of the exposed oxide sidewall.

Although the SEM images in FIG. 11 demonstrate the feasibility of placing capture nanoparticles (C-NPs) on the desired positions, finding optimum experimental parameters for real sensor geometry is not trivial. This is because the free energies of interaction (or force) between a C-NP and the substrate surface (in the colloidal environment) depend on many parameters such as the ion concentration, surface potentials of the C-NP and SAMs-functionalized surfaces, C-NP diameter, and the sensor geometry. To aid in solving this problem, a procedure for calculating electrostatic potentials and forces, involving numerically solving Poisson-Boltzmann equations, has been established. An example of such a calculation (for electrostatic potentials and electrostatic fields for a drain/dielectric/source geometry) is shown in FIG. 12.

Example 3

Formation of Nanoparticle Satellites Via DNA Hybridization (Step c in FIG. 9)

In the biosensor of the inventor, the presence of single-stranded oligonucleotide target (t-ssDNA) molecules leads to, through DNA hybridization (FIG. 9(e)), the formation of nanoparticle satellites (NP-SATs) around the C-NPs, FIG. 9(c). The important feature of the approach is that the DNA hybridization is carried out only on C-NPs. For this exclusive hybridization to be successful, it is essential that when migrating DNA molecules impinge on any surface except for that of C-NPs, they should not be adsorbed, but returned back into the solution so that they remain available for hybridization. Since DNA molecules are negatively charged, undesired adsorption can be prevented by passivating the silicon oxide surface using negatively-charged or non-polar molecules. There are a number of approaches for passivating the silicon oxide surface and forming NP-SATs around the C-NPs, such as those shown in FIG. 13. The source and drain electrodes (Au), on the other hand, are functionalized with 16-mercaptohexadecanoic acid (MHA; —COO— terminated; negatively charged), which repel DNA molecules.

For the first approach, Scheme 1 (top in FIG. 13), a silicon oxide surface is functionalized with SAMs of APTES (—$NH_3$ terminated; positively charged). Immersion of the wafer into a colloid containing C-NPs (Au nanoparticles (AuNPs); negatively charged) leads to attachment of C-NPs on the APTES functionalized surface, FIG. 13-S1(a). Then, the terminating amine group (—$NH_3^+$) of APTES SAMs is modified by reacting with acetic acid ($CH_3COOH$), producing a surface terminated by methyl groups ~(—$CH_3$; non-polar), FIG. 13-S1(b). The methyl terminated surface provides the passivation, and when c-ssDNA molecules are introduced they are immobilized on the C-NP surface (Au) due to the chemical bonding between thiol (—SH) group of the c-ssDNA and the Au surface of the C-NP, FIG. 13-S1(c). (The structure of thiol modified c-ssDNA is shown in FIG. 15.) At this point, the device is ready for further DNA hybridization, with the procedure in FIG. 9(e), to produce NP-SATs/C-NP conjugates, FIG. 13 (the rightmost).

Another approach, Scheme 2 (bottom in FIG. 13), may also be used. The main difference from the previous approach is that c-ssDNA molecules are pre-attached to C-NPs prior to placing the C-NPs on the silicon oxide surface. As in the previous, ATPES SAMs are selectively formed on the silicon oxide surface, FIG. 13 (the leftmost). A solution containing c-ssDNA/C-NPs is prepared and brought into a contact with the silicon oxide surface, and the c-ssDNA/C-NPs attach on the APTES surface, FIG. 13-S2(a). Then, the amine group of APTES SAMs will be reacted with PITC (phenyl isothiocyanate; $C_6H_5NCS$), passivating the silicon oxide surface with negatively charged benzene group, FIG. 13-52(*b*). (Here, PITC is used because PITC solution does not degrade DNA, whereas acetic acid solution does.)

To test the feasibility of the above schemes, the following two preliminary experiments were carried out: a) surface passivation and b) formation of NP-SATs in a solution phase.

Surface Passivation

To check if the passivation schemes in FIG. 13 work, experiments were carried out on blanket silicon oxide wafers as follows. The silicon oxide surface was functionalized with APTES SAMs, then immersed the wafers into a colloid of ~50 nm AuNPs (C-NPs), resulting in attachment of C-NPs on the silicon oxide surface. For one wafer, the amine terminated silicon oxide surface was converted to methyl-terminated (non-polar) surface (Scheme 1) and for the other, to benzene-terminated (negatively charged) surface (Scheme 2). Both passivations prevent the attachment of negatively charged entities such as DNA and negatively-charged nanoparticles. This was tested by immersing the wafers into a colloid containing negatively charged ~20 nm AuNPs. SEM images in FIG. 14 demonstrate that both passivations worked pretty well; no ~20 nm AuNP was attached on the passivated surfaces, while for control samples (no passivation step) the surfaces were saturated with ~20 nm AuNPs.

Formation of NP-SATs Around C-NPs in a Solution Phase

Another critical step for the proposed DNA sensor is the formation of NP-SATs around C-NPs via DNA hybridization. Fortunately, the formation of nanoparticle satellites or nanoparticle networks/crystals via DNA hybridization has been demonstrated by others in a solution environment (homogeneous hybridization). See, for example:

1. X. Y. Xu, N. L. Rosi, Y. H. Wang, F. W. Huo, C. A. Mirkin. Asymmetric functionalization of gold nanoparticles with oligonucleotides. *Journal of American Chemical Society*, 128, 9286 (2006).
2. F. W. Huo, A. K. R. Lytton-Jean, C. A. Mirkin. Asymmetric functionalization of nanoparticles based on thermally addressable DNA interconnects. *Advanced Materials*, 18, 2304 (2006).
3. R. C. Mucic, J. J. Storhoff, C. A. Mirkin, R. L. Letsinger. DNA-directed synthesis of binary nanoparticle network materials. *Journal of American Chemical Society*, 120, 12674 (1998).

Built on these studies, the formation of NP-SATs were tested, also in a solution phase, using ~50 nm AuNPs as C-NPs, ~20 nm AuNPs as the satellite nanoparticles, and DNA sequences for single-stranded capture DNA (c-ssDNA), single-stranded target DNA (t-ssDNA), and single-stranded probe DNA (p-ssDNA), as shown in FIG. 15. The experiment followed the procedure shown in FIG. 9(*e*). FIG. 15(*a*) displays an SEM image demonstrating successful formation of NP-SATs on a C-NP. For the control sample, which underwent exactly the same procedure except for no exposure to t-ssDNA, no NP-SAT was found, FIG. 15(*b*).

These two experiments, demonstrating the surface passivation and formation of NP-SATs, provide a fundamental framework to realize exclusive DNA hybridization and NP-SAT formation on the surface of C-NPs, leading to the configuration in FIG. 9(*c*).

Example 4

Electrical Detection (Step d in FIG. 9)

Once the formation of NP-SATs on C-NPs is completed (FIG. 9(*c*)), the sensor is ready for electrical measurement, FIG. 9(*d*). Although the measurement can be done in-situ while the solution is in contact with the sensor, which might also provide additional information beyond t-ssDNA detection (such as hybridization kinetics), ex-situ measurement was pursued since it is simpler and robust. The sample preparation for ex-situ I-V measurement involves rinsing with washing buffer/DI wafer and drying in a $N_2$ stream. Once the sample is dried, the NP-SAT/C-NP structure is expected to be fairly robust, meaning that the structural integrity of the NP-SATs will remain intact for further chemical and/or mechanical treatments such as UV ozone, oxygen plasma, and routine wafer handling. This is based on preliminary experiments on blanket wafers, which showed no sign of structural disintegration of NP-SATs/C-NP conjugates after UV ozone treatment and wafer handling.

The electrical current flow in our nanoparticle bridge DNA sensor can occur in many ways:
1. quantum mechanical electron tunneling;
2. conventional current flow through direct physical contact between C-NP and satellite NPs as well as between the satellite NPs and the electrodes;
3. electron transfer along the DNA chains, and
4. combinations of the above.

The dominant conduction mechanism will depend on the sample preparation and will explore process options to most reliable I-V reading. For example, one option is to remove DNA molecules in the NP-SATs/C-NP conjugates using UV ozone or oxygen plasma treatment, followed by rinsing and drying. During the removal of the DNA molecules, the C-NP and satellite NPs are likely to be brought into a direct physical contact due to van der Waals attraction, which may lead to conventional current flow between the nanoparticles. In other considerations, the relative sizes of the C-NPs and satellite NPs may affect the current flow, FIG. 16. For example, the configurations in FIG. 16(*b*) and (*c*) have more chance to produce a direct physical contact between a satellite NP and an electrode, leading to conventional electrical current flows across these contacts.

There is a correlation between t-ssDNA concentration and output current with t-ssDNA concentration increasing the number of NP-SATs/C-NP conjugates that successfully bridge the source/drain electrodes. The number of the pre-positioned C-NPs (FIG. 9(*b*)) is another factor that must be optimized.

Example 5

Electric Detection in Planar Device

A biosensor device with a planar design for the source/dielectric/drain stack was prepared as shown in the schematic in FIG. 6, having a capture unit with a single-stranded oligonucleotide with perfect complementarity to the target DNA. In addition, a control device with a planar design for the source/dielectric/drain stack was prepared as shown in the schematic in FIG. 7, having a capture unit with a single-stranded oligonucleotide without perfect complementarity to the target DNA. Scanning electron micrograph (SEM) images were taken for the device having perfect complementarity to the target DNA and for the device lacking perfect complementarity to the target DNA (mismatched; control).

FIG. 6 also shows scanning electron micrograph (SEM) images of the device of the invention, when exposed to target DNA with perfect complementarity to the single-stranded oligonucleotide of the capture unit.

FIG. 7 also shows scanning electron micrograph (SEM) images of a control device, when exposed to target DNA lacking perfect complementarity (mismatched; control) to the single-stranded oligonucleotide of the capture unit.

FIG. 8 is an I-V plot of current (in μA) as a function of applied voltage (in mV) for target DNA with perfect complementarity to the single-stranded oligonucleotide of the capture unit and for target DNA lacking perfect complementarity (mismatched; control) to the single-stranded olignonucleotide of the capture unit, establishing the ability to detect the perfect complementarity electrically.

FIG. 17 is a schematic diagram of an alternate embodiment of the device of the invention with a planar design in which the source and drain electrodes are separated by dielectric material, including an exploded view of the capture unit with satellite nanoparticles and a photograph of the same.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A device, comprising:
an electrically-insulating substrate; and
a first detecting unit, comprising:
- a source electrode disposed on said electrically-insulating substrate;
- a drain electrode; and
- a dielectric layer having a substantially uniform thickness and at least one exposed side;
- wherein said dielectric layer is disposed between said source electrode and said drain electrode;
- wherein said dielectric layer is contiguous with said drain electrode;
- wherein said source electrode, said drain electrode and said dielectric layer are self aligned on said at least one exposed side of said dielectric layer;
- a first self-assembling monolayer attached to and in contact with said at least one exposed side of said dielectric layer;
- a second self-assembling monolayer attached to and in contact with said source electrode and said drain electrode;
- wherein said second self-assembling monolayer has a polarity different than the polarity of said first self-assembling monolayer; and
- at least one capture unit, comprising:
  - a nanoparticle; and
  - a plurality of first single-stranded oligonucleotides attached to said nanoparticle;
  - wherein said first single-stranded oligonucleotides have a first nucleotide sequence complementary to a portion of a first oligonucleotide target; and
  - wherein said capture unit is located on said exposed side of said dielectric layer and is substantially centered between said source electrode and said drain electrode.

2. A device of claim 1, further comprising:
a plurality of second detecting units, each second detecting unit comprising:
- a source electrode disposed on said electrically-insulating substrate;
- a drain electrode; and
- a dielectric layer having a substantially uniform thickness and at least one exposed side;
- wherein said dielectric layer is disposed between said source electrode and said drain electrode;
- wherein said dielectric layer is contiguous with said drain electrode;
- wherein said source electrode, said drain electrode and said dielectric layer are self aligned on said at least one exposed side of said dielectric layer;
- a first self-assembling monolayer attached to and in contact with said at least one exposed side of said dielectric layer;
- a second self-assembling monolayer attached to and in contact with said source electrode and said drain electrode;
- wherein said second self-assembling monolayer has a polarity different than the polarity of said first self-assembling monolayer; and
- at least one capture unit, comprising:
  - a nanoparticle; and
  - a plurality of at least one second single-stranded oligonucleotides attached to said nanoparticle;
  - wherein said at least one second single-stranded oligonucleotides have a second nucleotide sequence complementary to a portion of a second oligonucleotide target;
  - wherein said capture unit is located on said exposed side of said dielectric layer and is substantially centered between said source electrode and said drain electrode;
  - wherein said second nucleotide sequences are the same or different from said first nucleotides sequences in said first detecting unit; and
  - wherein said second nucleotide sequences are the same or different from other second nucleotide sequences in said plurality of second detecting units.

3. A device of claim 1,
wherein said nanoparticle is a metal, semiconductor, or magnetic colloidal particle.

4. A device of claim 1,
wherein said electrically-insulating substrate is silicon, silicon dioxide, or a combination thereof.

5. A device of claim 4,
wherein said electrically-insulating substrate comprises more than one layer.

6. A device of claim 1,
wherein said source and drain electrodes comprise a metal selected from the group consisting of gold, silver, titanium, copper, or a combination thereof.

7. A device of claim 1, further comprising:
a plurality of microfluidic channels; and
an optional cover.

8. A device of claim 1,
wherein said source electrode, said drain electrode and said dielectric layer are self aligned on said at least one exposed side of said dielectric layer in a vertical dimension.

9. A device, comprising:
an electrically-insulating substrate; and
a first detecting unit, comprising:
a source electrode disposed on said electrically-insulating substrate;
a drain electrode; and
a dielectric layer having a substantially uniform thickness and at least one exposed side;
wherein said dielectric layer is disposed between said source electrode and said drain electrode;
wherein said source electrode, said drain electrode and said dielectric layer are in the same plane;
a first self-assembling monolayer attached to and in contact with said dielectric layer;
a second self-assembling monolayer attached to and in contact with said source electrode and said drain electrode;
wherein said second self-assembling monolayer has a polarity different than the polarity of said first self-assembling monolayer; and at least one capture unit, comprising:
a nanoparticle; and
a plurality of first single-stranded oligonucleotides attached to said nanoparticle;
wherein said first single-stranded oligonucleotides have a first nucleotide sequence complementary to a portion of a first oligonucleotide target; and
wherein said capture unit is located on said dielectric layer and is substantially centered between said source electrode and said drain electrode.

10. A system, comprising:
a device of claim 1; and
a plurality of nanoparticle reporter conjugates;
wherein said nanoparticle reporter conjugates comprise at least one nanoparticle and a single-stranded oligonucleotide complementary to at least a portion of said first oligonucleotide target different than said portion complementary to said first nucleotide sequence; and
wherein said nanoparticle is a metal, semiconductor, or magnetic colloidal particle.

11. A system, comprising:
a device of claim 2; and
a plurality of first nanoparticle reporter conjugates; and
a plurality of at least one second nanoparticle reporter conjugates;
wherein said first nanoparticle reporter conjugates comprise at least one nanoparticle and a single-stranded oligonucleotide complementary to at least a portion of said first oligonucleotide target different than said portion complementary to said first nucleotide sequence;
wherein said nanoparticle in said first nanoparticle reporter conjugate is a metal, semiconductor, or magnetic colloidal particle;
wherein said at least one second nanoparticle reporter conjugates comprise at least one nanoparticle and a single-stranded oligonucleotide complementary to at least a portion of said at least one second oligonucleotide target different than said portion complementary to said at least one second nucleotide sequence;
wherein said nanoparticle in said at least one second nanoparticle reporter conjugate is a metal, semiconductor, or magnetic colloidal particle;
wherein said second nanoparticle reporter conjugates are the same or different from said first nanoparticle reporter conjugates; and
wherein said second nanoparticle reporter conjugates are the same or different from said other second nanoparticle reporter conjugates.

12. A system of claim 10, further comprising:
an electrical reading device for interrogating said device.

13. A system of claim 12,
wherein said electrical reading device is portable.

14. A method for detecting nucleic acid hybridization, comprising:
providing a device of claim 1;
passivating said first self-assembling monolayer;
providing a solution comprising at least one buffer and single-stranded oligonucleotide target under hybridizing conditions;
wherein said single-stranded oligonucleotide target hybridizes a portion of said first nucleotide sequence thereby leaving an unhybridized portion of said single-stranded oligonucleotide target;
providing a plurality of first nanoparticle reporter conjugates under hybridizing conditions;
wherein said first nanoparticle reporter conjugates comprise at least one nanoparticle and an oligonucleotide complementary to said unhybridized portion of said single-stranded oligonucleotide target;
wherein said nanoparticle in said first nanoparticle reporter conjugate is a metal, semiconductor, or magnetic colloidal particle;
applying a voltage drop across said electrodes; and
measuring a change in conductivity, resistivity, capacitance, or impedance across said electrodes at known locations to determine perfect complementarity of said oligonucleotide target to said first oligonucleotide sequence.

15. A method of claim 14,
wherein said measuring step measures an increase in conductivity across said electrodes at known locations to determine perfect complementarity of said oligonucleotide target to said first oligonucleotide sequence.

16. A method of claim 14,
wherein said single-stranded oligonucleotide target is prepared by heating a solution comprising double-stranded oligonucleotide target.

17. A method of claim 14, further comprising:
washing to remove unhybridized components from said detecting unit.

18. A method of claim 14, further comprising:
heating a solution comprising double stranded oligonucleotide target to form said solution comprising single-stranded oligonucleotide target.

19. A method for detecting nucleic acid hybridization, comprising:
providing a device of claim 2;
passivating said first self-assembling monolayer;
providing a solution comprising at least one buffer and single-stranded oligonucleotide target under hybridizing conditions;
wherein said single-stranded oligonucleotide target hybridizes a portion of said at least one second nucleotide sequence thereby leaving an unhybridized portion of said single-stranded oligonucleotide target;
providing a plurality of at least one second nanoparticle reporter conjugates under hybridizing conditions;
wherein said second nanoparticle reporter conjugates comprise at least one nanoparticle and an oligonucleotide complementary to said unhybridized portion of said single-stranded oligonucleotide target;
wherein said nanoparticle in said second nanoparticle reporter conjugate is a metal, semiconductor, or magnetic colloidal particle;
wherein said second nanoparticle reporter conjugates are the same or different from said first nanoparticle reporter conjugates;
wherein said second nanoparticle reporter conjugates are the same or different from said other second nanoparticle reporter conjugates;
wherein said measuring step is carried out in parallel or sequentially for said first detecting unit and said plurality of said additional detecting units.

20. A process for preparing a nano-scale bridging biosensor, comprising:
forming a device, comprising:
an electrically-insulating substrate; and
a first detecting unit, comprising:
a source electrode disposed on said electrically-insulating substrate;
a drain electrode; and
a dielectric layer having a substantially uniform thickness and at least one exposed side;

a first self-assembling monolayer attached to and in contact with said at least one exposed side of said dielectric layer;

a second self-assembling monolayer attached to and in contact with said source electrode and said drain electrode;

wherein said second self-assembling monolayer has a polarity different than the polarity of said first self-assembling monolayer;

wherein said dielectric layer is disposed between said source electrode and said drain electrode;

wherein said dielectric layer is contiguous with said drain electrode; and wherein said source electrode, said drain electrode and said dielectric layer are self aligned on said at least one exposed side of said dielectric layer;

providing on said exposed side of said dielectric layer and substantially centered between said source electrode and said drain electrode at least one capture unit, said capture unit comprising:
- a nanoparticle; and
- a plurality of first single-stranded oligonucleotides attached to said nanoparticle; and
- wherein said first single-stranded oligonucleotides have a first nucleotide sequence complementary to a portion of a first oligonucleotide target; and passivating said first self-assembling monolayer.

21. A process of claim 20, wherein said first single-stranded oligonucleotides are attached to said nanoparticle prior to attachment of said capture unit to said exposed side of said dielectric layer.

22. A process of claim 20, wherein said first single-stranded oligonucleotides are attached to said nanoparticle subsequent to attachment of said capture unit to said exposed side of said dielectric layer.

23. A process of claim 20, wherein said self-assembling monolayer is passivated.

24. A device, comprising:

an electrically-insulating substrate; and a first detecting unit, comprising:
- a source electrode disposed on said electrically-insulating substrate;
- a drain electrode; and
- a dielectric layer having a substantially uniform thickness and at least one exposed side;
- wherein said dielectric layer is disposed between said source electrode and said drain electrode;
- wherein said dielectric layer is contiguous with said drain electrode;
- wherein said source electrode, said drain electrode and said dielectric layer are self aligned on said at least one exposed side of said dielectric layer;
- a first self-assembling monolayer attached to and in contact with said at least one exposed side of said dielectric layer;
- a second self-assembling monolayer attached to and in contact with said source electrode and said drain electrode;
- wherein said second self-assembling monolayer has a polarity different than the polarity of said first self-assembling monolayer; and
- at least one capture unit, comprising:
  - a nanoparticle; and
  - a plurality of first antibodies attached to said nanoparticle;
  - wherein said first antibody have affinity to a portion of a first polypeptide target; and
  - wherein said capture unit is located on said exposed side of said dielectric layer and is substantially centered between said source electrode and said drain electrode.

25. A method of detecting protein-antibody interaction, comprising:

providing a device of claim 24;

passivating said first self-assembling monolayer;

providing a solution comprising at least one buffer and polypeptide target under binding conditions;
- wherein a portion of said polypeptide target binds said first antibody;

providing a plurality of first nanoparticle reporter conjugates under hybridizing conditions;
- wherein said first nanoparticle reporter conjugates comprise at least one nanoparticle and a second antibody capable of binding the unbound portion of said polypeptide target;
- wherein said nanoparticle in said first nanoparticle reporter conjugate is a metal, semiconductor, or magnetic colloidal particle;

applying a voltage drop across said electrodes; and measuring a change in conductivity, resistivity, capacitance, or impedance across said electrodes at known locations to determine perfect binding of said polypeptide target to said first antibody.

* * * * *